US008603078B2

(12) United States Patent
Stefanchik et al.

(10) Patent No.: US 8,603,078 B2
(45) Date of Patent: Dec. 10, 2013

(54) METHODS AND DEVICES FOR GUIDING AND SUPPORTING SURGICAL INSTRUMENTS

(75) Inventors: David Stefanchik, Morrow, OH (US); James T. Spivey, Cincinnati, OH (US); Robert M. Trusty, Cincinnati, OH (US); Peter K. Shires, Hamilton, OH (US); Michael J. Stokes, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 427 days.

(21) Appl. No.: 12/903,330

(22) Filed: Oct. 13, 2010

(65) Prior Publication Data
US 2012/0095449 A1    Apr. 19, 2012

(51) Int. Cl.
*A61B 17/00* (2006.01)

(52) U.S. Cl.
USPC ............................. 606/1; 606/130; 600/102

(58) Field of Classification Search
USPC ...................................... 606/1, 130; 600/102
See application file for complete search history.

(56) References Cited

U.S. PATENT DOCUMENTS

| | | |
|---|---|---|
| 4,022,191 A | 5/1977 | Jamshidi |
| 4,608,977 A | 9/1986 | Brown |
| 4,809,694 A | 3/1989 | Ferrara |
| 5,031,634 A | 7/1991 | Simon |
| 5,053,042 A | 10/1991 | Bidwell |
| 5,100,387 A | 3/1992 | Ng |
| 5,197,971 A | 3/1993 | Bonutti |
| 5,199,419 A | 4/1993 | Remiszewski et al. |
| 5,201,742 A * | 4/1993 | Hasson .......................... 606/130 |
| 5,235,987 A | 8/1993 | Wolfe |
| 5,271,385 A | 12/1993 | Bailey |
| 5,316,014 A | 5/1994 | Livingston |
| 5,320,111 A | 6/1994 | Livingston |

(Continued)

FOREIGN PATENT DOCUMENTS

| | | |
|---|---|---|
| DE | 82 16 373 U1 | 7/1982 |
| WO | WO-0217810 A2 | 3/2002 |

(Continued)

OTHER PUBLICATIONS http://www.innomedic.de/en/products/innomotion_overview.php (Innomedic Products), accessed Oct. 24, 2006.

(Continued)

*Primary Examiner* — Sam Yao
*Assistant Examiner* — Michael M Kim
(74) *Attorney, Agent, or Firm* — Nutter McClennen & Fish LLP

(57) ABSTRACT

Methods and devices are provided for allowing a surgical instrument to be supported by a surgical support system configured to controllably guide the instrument to a desired position at surgical site. A surgical support system is provided that includes a guide port defining a pivot point about which a surgical instrument advance therethrough can pivot. The guide port, and hence the pivot point, can be located a distance above a tissue surface through which the instrument is advanced. Methods and devices are also provided for allowing insufflation of a body cavity without introduction of an insufflation fluid therein. A mechanical insufflation device is provided that includes an expandable distal member configured to selectively expand and unexpand to mechanically insufflate a body cavity. The mechanical insufflation device can optionally be used with the surgical support system.

16 Claims, 13 Drawing Sheets

(56) References Cited

U.S. PATENT DOCUMENTS

| | | | |
|---|---|---|---|
| 5,345,927 A * | 9/1994 | Bonutti | 600/207 |
| 5,361,752 A | 11/1994 | Moll et al. | |
| 5,494,039 A | 2/1996 | Onik et al. | |
| 5,647,373 A | 7/1997 | Paltieli et al. | |
| 5,690,606 A | 11/1997 | Slotman | |
| 5,800,394 A | 9/1998 | Yoon et al. | |
| 5,868,673 A | 2/1999 | Vesely | |
| 5,911,707 A | 6/1999 | Wolvek et al. | |
| 5,916,175 A | 6/1999 | Bauer et al. | |
| 5,941,889 A | 8/1999 | Cermak | |
| 5,954,670 A | 9/1999 | Baker | |
| 5,984,930 A | 11/1999 | Maciunas et al. | |
| D422,706 S | 4/2000 | Bucholz et al. | |
| 6,048,321 A | 4/2000 | McPherson et al. | |
| 6,110,182 A | 8/2000 | Mowlai-Ashtiani | |
| 6,146,401 A | 11/2000 | Yoon et al. | |
| 6,195,577 B1 | 2/2001 | Truwit et al. | |
| 6,203,499 B1 | 3/2001 | Imling et al. | |
| 6,216,029 B1 | 4/2001 | Paltieli et al. | |
| 6,231,565 B1 | 5/2001 | Tovey et al. | |
| 6,231,585 B1 | 5/2001 | Takahashi et al. | |
| 6,236,875 B1 | 5/2001 | Bucholz et al. | |
| 6,245,028 B1 | 6/2001 | Furst et al. | |
| 6,248,062 B1 | 6/2001 | Adler et al. | |
| 6,283,942 B1 | 9/2001 | Staehlin et al. | |
| 6,361,499 B1 | 3/2002 | Bates et al. | |
| 6,379,307 B1 | 4/2002 | Filly et al. | |
| 6,400,979 B1 | 6/2002 | Stoianovici et al. | |
| 6,443,960 B1 | 9/2002 | Brabrand et al. | |
| 6,445,943 B1 | 9/2002 | Ferre et al. | |
| 6,468,226 B1 | 10/2002 | McIntyre, IV | |
| 6,475,152 B1 | 11/2002 | Kelly, Jr. et al. | |
| 6,490,467 B1 | 12/2002 | Bucholz et al. | |
| 6,501,981 B1 | 12/2002 | Schweikard et al. | |
| 6,529,765 B1 | 3/2003 | Franck et al. | |
| 6,535,756 B1 | 3/2003 | Simon et al. | |
| 6,546,279 B1 | 4/2003 | Bova et al. | |
| 6,547,786 B1 | 4/2003 | Goble | |
| 6,665,554 B1 | 12/2003 | Charles et al. | |
| 6,687,531 B1 | 2/2004 | Ferre et al. | |
| 6,723,106 B1 | 4/2004 | Charles et al. | |
| 6,731,966 B1 | 5/2004 | Spigelman et al. | |
| 6,770,027 B2 | 8/2004 | Banik et al. | |
| 6,782,288 B2 | 8/2004 | Truwit et al. | |
| 6,783,524 B2 | 8/2004 | Anderson et al. | |
| 6,785,572 B2 | 8/2004 | Yanof et al. | |
| 6,807,965 B1 | 10/2004 | Hickle | |
| 6,813,520 B2 | 11/2004 | Truckai et al. | |
| 6,966,876 B2 | 11/2005 | Irion et al. | |
| 7,021,173 B2 | 4/2006 | Stoianovici et al. | |
| 7,201,734 B2 | 4/2007 | Hickle | |
| 7,247,154 B2 | 7/2007 | Hickle | |
| 7,347,862 B2 | 3/2008 | Layer | |
| 7,470,252 B2 | 12/2008 | Mickley et al. | |
| 7,615,005 B2 | 11/2009 | Stefanchik et al. | |
| 2003/0023260 A1 | 1/2003 | Bonutti | |
| 2003/0100814 A1 | 5/2003 | Kindlein | |
| 2003/0208207 A1 | 11/2003 | Layer | |
| 2003/0229338 A1 | 12/2003 | Irion et al. | |
| 2004/0138525 A1 | 7/2004 | Saadat et al. | |
| 2005/0075540 A1 | 4/2005 | Shluzas et al. | |
| 2005/0096502 A1 | 5/2005 | Khalili | |
| 2006/0042636 A1 | 3/2006 | Nalagatla et al. | |
| 2006/0229641 A1 | 10/2006 | Gupta et al. | |
| 2007/0021656 A1 | 1/2007 | Martin et al. | |
| 2008/0200762 A1 | 8/2008 | Stokes et al. | |
| 2009/0187074 A1 | 7/2009 | Saadat et al. | |
| 2009/0227843 A1 | 9/2009 | Smith et al. | |
| 2009/0326462 A1 * | 12/2009 | Wingardner et al. | 604/164.09 |
| 2010/0042097 A1 * | 2/2010 | Newton et al. | 606/41 |
| 2010/0057008 A1 | 3/2010 | Solar | |
| 2010/0106052 A1 | 4/2010 | Uznanski et al. | |
| 2010/0113886 A1 | 5/2010 | Piskun et al. | |
| 2012/0035502 A1 | 2/2012 | Menegazzi | |

FOREIGN PATENT DOCUMENTS

| | | |
|---|---|---|
| WO | WO-03067341 A2 | 8/2003 |
| WO | WO-03091839 A2 | 11/2003 |
| WO | 2007/109554 A2 | 9/2007 |

OTHER PUBLICATIONS http://www.intuitivesurgical.com/products/index.aspx (Intuitive Surgical Products), accessed Oct. 24, 2006.

http://www.lap-laser.com/e/laser_m/prod/med.html (LAP Laser Application), accessed Oct. 24, 2006.

Maurin, et al., "A new robotic system for CT-guided percutaneous procedures with haptic feedback," LSIIT (UMR CNRS-ULP 7005), Louis Pasteur University, Bd. S. Brant, BP 10413, Strasbourg Illkirch 67412, France.

Maurin, et al., "A Parallel 5 DOF Positioner for Semi-Spherical Workspaces", Proceedings of DETC'04, ASME 2004 Design Engineering Technical Conferences and Computers and Information in Engineering Conference, Sep. 28-Oct. 2, 2004, Salt Lake City Utah USA.

Maurin, et al., "A Parallel Robotic System with Force Sensors for Percutaneous Procedures Under CT-Guidance", LSIIT (UMR CNRS-ULP 7005), Strasbourg I University Bd. S. Brant, BP 10413, 67412 Illkirch cedex, France.

Stoianovici, et al., "A Novel Mechanical Transmission Applied to Percutaneous Renal Access", DSC—vol. 61, Proceedings of the ASME Dynamic Systems and Control Division 1997.

U.S. Appl. No. 12/903,645, filed Oct. 13, 2010.

URobitics, Brady Urological Institute, Johns Hopkins Medical Institutions, "Z-Stage PAKY", date of publication unknown but no later than Oct. 26, 2006 (date of citation in U.S. Appl. No. 11/307,231).

URobotics, Brady Urological Institute, Johns Hopkins Medical Institutions, "PAKY Needle Driver," date of publication unknown but no later than Oct. 26, 2006 (date of citation in U.S. Appl. No. 11/307,231).

URobotics, Brady Urological Institute, Johns Hopkins Medical Institutions, "The RCM Robot", date of publication unknown but no later than Oct. 26, 2006 (date of citation in U.S. Appl. No. 11/307,231).

International Search Report for Application No. PCT/US2011/055957, issued Jan. 13, 2012. (6 pages).

* cited by examiner

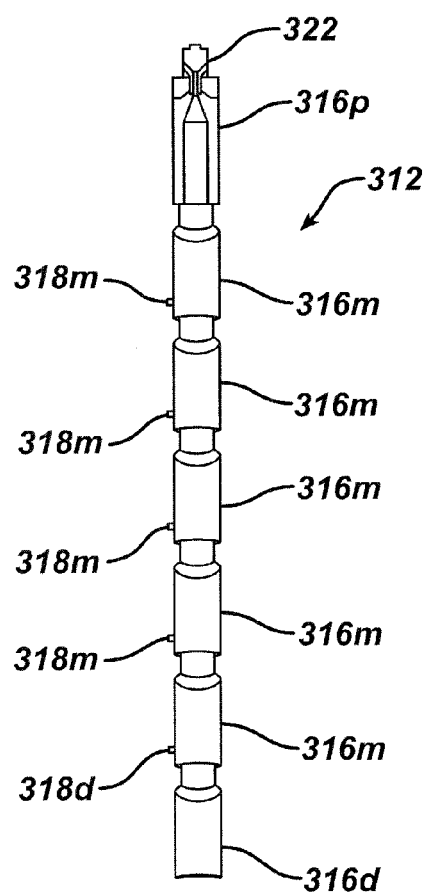
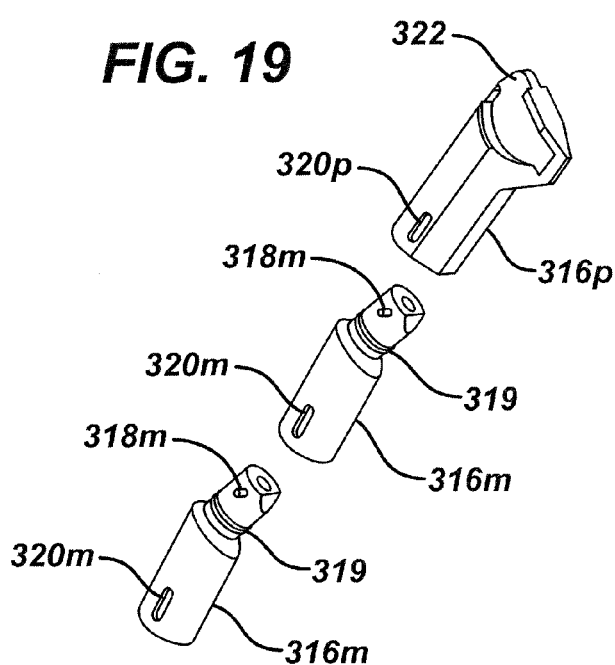
FIG. 18
FIG. 19

METHODS AND DEVICES FOR GUIDING AND SUPPORTING SURGICAL INSTRUMENTS

FIELD OF THE INVENTION

The present invention relates to methods and devices for performing minimally invasive surgical procedures.

BACKGROUND OF THE INVENTION

Abdominal laparoscopic surgery gained popularity in the late 1980s, when benefits of laparoscopic removal of the gallbladder over traditional (open) surgery became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

In laparoscopic abdominal procedures for example, the abdominal cavity is generally insufflated with $CO_2$ gas to a pressure of around 15 mm Hg. Insufflation generally provides adequate space within the abdominal cavity to visualize and work therein. However, insufflation hinders if not entirely prevents a patient from breathing on their own. Thus, a patient is typically sedated and put on a ventilator during a surgical procedure involving insufflation despite the risk of one or more complications that can arise from sedation and artificial respiration, e.g., adverse reaction to sedation drugs, apnea, hypotension, aggravation of a pre-existing condition such as a heart defect, etc.

The abdominal wall is pierced, usually following insufflation of the abdominal cavity, and one or more laparaoscopic instruments are inserted into the abdominal cavity, either directly or through one or more cannulas. A laparoscopic telescope connected to an operating room monitor can be used to visualize the operative field and can be placed through one of the cannulas. Other laparoscopic instruments such as graspers, dissectors, scissors, retractors, etc. can be placed through the other cannula(s) to facilitate various manipulations by the surgeon. It can be difficult for a single medical professional to handle numerous surgical instruments simultaneously inserted into a patient. However, having multiple medical professionals handle various instruments simultaneously inserted into a patient can crowd the surgical space and can increase the complexity of manipulating multiple instruments in an effective cooperative relationship at the surgical site. These problems can unduly lengthen the duration of the surgery, potentially increasing the risk of patient complications.

Moreover, if an instrument needs to be held in a static position, e.g., to provide stable visualization of a surgical site, to retract tissue away from a surgical site while another instrument(s) performs another aspect of the surgical procedure at the surgical site, etc., it can be difficult to hold the instrument steady by hand.

Accordingly, there is a need for methods and devices which allow laparoscopic procedures to be performed with an enhanced ability to access a surgical site and to position and visualize surgical instruments at the surgical site.

SUMMARY OF THE INVENTION

The present invention generally provides methods and devices for performing minimally invasive surgical procedures. In one embodiment, a surgical device is provided that includes an elongate member and a plurality of arms. The elongate member has at least one lumen between proximal and distal ends thereof, and has a hub formed at the distal end. The plurality of arms each have a proximal end coupled to the hub. The arms are each configured to move between an unexpanded configuration in which the arm is substantially straight such that the arms are substantially parallel to one another, and an expanded configuration in which the arm is articulated such that the arms define a working space therebetween. The arms are configured to be locked in the expanded configuration.

The arms can have a variety of configurations. When the arms are in the unexpanded configuration, the arms can be substantially parallel to one another, and when the arms are in the expanded configuration, the arms can be articulated relative to one another to define the working space. The arms can each include a plurality of segments configured to move relative to one another. When the arms are in the unexpanded configuration, the segments of each arm can be substantially longitudinally aligned such that the arms are substantially parallel to one another, and when the arms are in the expanded configuration, the segments of each arm can be articulated relative to one another.

The working space can also have a variety of configurations. The arms in the expanded configuration can define a working space having any shape, such as a substantially spherical working space. The working space can have a diameter greater than a diameter of the at least one lumen at the hub.

The surgical device can have any number of variations. For example, the device can include a flexible cover disposed around the plurality of arms. The cover can be configured to move between a relaxed configuration corresponding to the arms being in the unexpanded configuration, and a flexed configuration corresponding to the arms being in the expanded configuration. For another example, the lumen can be configured to slidably receive a surgical instrument therein such that a distal end of the instrument can be positioned and maneuvered within the working space when the arms are in the expanded configuration.

The device can include an actuator configured to move the arms between the unexpanded and expanded configurations. The actuator can include at least one cable extending along a length of the elongate member. In one embodiment, the at least one cable can include a plurality of cables that are equally spaced apart from one another around a circumference of the elongate member. The device can optionally include a lock mechanism configured to engage the at least one cable to lock the at least one cable in a fixed position to lock the arms in the expanded configuration.

In another aspect, a surgical system is provided that includes a surgical instrument and a mechanical insufflation device that includes an elongate member and a plurality of arms. The elongate member has proximal and distal ends, and has an inner lumen extending therethrough. The plurality of arms are coupled to and extend distally beyond the distal end of the member. Each of the arms have a distal end configured to move radially outward such that the arms are configured to move from an unexpanded configuration, in which the arms are substantially parallel to one another, to an expanded configuration, in which the distal ends of the arms are moved radially outward such that the arms are not parallel to one another, and such that the arms define a working space distal to the distal end of the shaft. The surgical instrument is configured to be inserted through the inner lumen of the shaft such that when the arms are in the expanded configuration, a distal end of the instrument exits the inner lumen and enters the working space.

The mechanical insufflation device can have a variety of configurations. The mechanical insufflation device can include a flexible cover disposed over the arms such that outward radial movement of the distal ends of the arms radially expands the cover to prevent matter from moving into void space between adjacent arms. The mechanical insufflation device can include an actuator configured to move the distal ends of the arms radially outward.

The surgical system can vary in any number of ways. In one embodiment, the surgical system can include a surgical support configured to be positioned external to an exterior tissue surface of a patient such that an instrument guide port of the surgical support system is positioned a distance remote from the tissue surface. The instrument guide port can be configured to slidably receive the mechanical insufflation device therethrough to guide the arms of the mechanical insufflation device into a body cavity underlying the tissue surface. The surgical support can optionally include a lock mechanism configured to lock the mechanical insufflation device in a fixed position relative to the support.

In another aspect, a surgical method is provided that includes providing a surgical device, advancing a distal portion of the device into a patient, and actuating the surgical device. The surgical device has an elongate member and a plurality of arms extending distally beyond a distal end of the member. The elongate member has an inner lumen extending therethrough, the arms are movable between unexpanded and expanded configurations, the arms in the unexpanded configuration occlude a distal end of the inner lumen, and the arms in the expanded configuration define a working space distal of the distal end of the inner lumen. The working space has a diameter greater than a diameter of the inner lumen. The distal portion of the device is advanced into the patient with the arms in the unexpanded configuration to position the arms within a body cavity and distal to an interior tissue surface facing the body cavity. Actuating the surgical device moves the arms from the unexpanded configuration to the expanded configuration, the arms pushing against the interior tissue surface to define a working space within the body cavity. In some embodiments, the arms of the surgical device can be locked in the expanded configuration.

The method can vary in any number of ways. For example, the surgical device can have a flexible cover disposed around the arms, and actuating the surgical device can cause the cover to flex radially outward, thereby preventing tissue from moving into void space between adjacent arms and into the working space. For another example, when the arms are in the expanded configuration, a surgical instrument can be inserted through the inner lumen to position a distal end of the surgical instrument within the working space. For yet another example, an insufflation fluid can be introduced into the body cavity.

In another embodiment, a surgical method is provided that includes positioning a surgical support system on an exterior tissue surface of a patient such that an instrument guide port of the surgical support system is positioned a distance remote from the tissue surface, advancing a surgical instrument through the instrument guide port such that a shaft of the surgical instrument extends through a tissue opening formed in the tissue surface to position a distal end of the instrument at a first position within a body cavity underlying the tissue surface, and manipulating the instrument. The instrument guide port defines a pivot point at the distance remote from the tissue surface. Manipulating the instrument pivots the instrument at the pivot point to move the distal end of the instrument from the first position within the body cavity to a second, different position within the body cavity. The second position can be at any location relative to the first position, such as being offset from the first position in at least two dimensions.

The instrument can be manipulated in any way. Manipulating the instrument can include moving the pivot point in at least two dimensions and/or can include forming the tissue opening with the distal end of the instrument.

The method can have any number of variations. For example, while the surgical support system remains in contact with the tissue surface, the instrument guide port can be moved to a different location such that the pivot point is located a second, different distance remote from the tissue surface. For another example, with the distal end of the instrument in one of the first and second positions, the instrument can be locked in a fixed position relative to the instrument guide port, thereby locking the distal end of the instrument in the one of the first and second positions. The distal end of the instrument locked in the one of the first and second positions can be prevented from moving in an x dimension and in a y dimension, and can be prevented from rotating about a longitudinal axis of the shaft of the instrument. For yet another example, when the distal end of the instrument is positioned within the body cavity, a volume of a working area within the body cavity can be increased by expanding a plurality of movable arms at the distal end of the instrument.

In another embodiment, a surgical method is provided that includes positioning a distal surface of a surgical support system in contact with a proximal skin surface of a patient such that a guide opening in a proximal portion of the system is positioned a distance proximal to the skin surface, advancing a surgical instrument through the guide opening to position a distal end of the instrument within a body cavity underlying the skin surface, and pivoting the instrument about a pivot point at a central longitudinal point of the guide opening to laterally and longitudinally reposition the distal end of the instrument within the body cavity. The guide opening is configured to slidably receive the surgical instrument therethrough. Pivoting the instrument about a pivot point can reposition the distal end of the instrument in any way, e.g., laterally reposition the distal end of the instrument in two dimensions. With the distal surface of the surgical support system remaining in contact with the proximal skin surface, the guide opening can optionally be moved to a different location such that the pivot point is located a second, different distance proximal to the skin surface.

In another aspect, a surgical method is provided that includes positioning a surgical support including distal and proximal portions movably coupled together on an exterior skin surface overlying a body cavity, inserting a surgical instrument through a guide in the proximal portion of the support and through an opening in the skin surface to position a distal end of the surgical instrument within the body cavity at a first location, and moving the proximal portion of the support relative to the distal portion of the support to move the distal end of the surgical instrument from the first location to a second, different location within the body cavity.

Moving the proximal portion of the support relative to the distal portion of the support can vary in any number of ways. For example, moving the proximal portion of the support can include moving the guide in an arcuate path along a diameter of the distal portion. For another example, moving the proximal portion of the support relative to the distal portion of the support can include moving the proximal portion in at least two dimensions relative to the distal portion, e.g., in three dimensions relative to the distal portion. For yet another example, moving the proximal portion of the support can include rotating the guide relative to the distal portion. The proximal portion of the support can include an arcuate support, and rotating the guide relative to the distal portion can include moving the guide in an arcuate path along the arcuate support. The distal portion can have a circular shape, and rotating the guide relative to the distal portion can include rotating the guide about a central axis of the distal portion. The central axis can be perpendicular to a diameter of the distal portion.

The method can vary in any number of ways. For example, with the distal end of the instrument in one of the first and second locations, the instrument can be locked in a fixed position relative to the guide, thereby locking the distal end of the instrument in the one of the first and second locations. For another example, a second surgical instrument can be optionally advanced through a second guide in the proximal portion of the support to advance a distal end of the second instrument through the opening in the skin surface and into the body cavity. Moving the proximal portion of the support can causes the distal end of the second instrument to move from a third location within the body cavity to a fourth, different location within the body cavity.

BRIEF DESCRIPTION OF THE DRAWINGS

The invention will be more fully understood from the following detailed description taken in conjunction with the accompanying drawings, in which:

FIG. 18 is a side view of one of the arms of the mechanical insufflation device of FIG. 15; and FIG. 19 is an exploded perspective view of a distal portion of one of the arms of the mechanical insufflation device of FIG. 15.

DETAILED DESCRIPTION OF THE INVENTION

Figure 1:
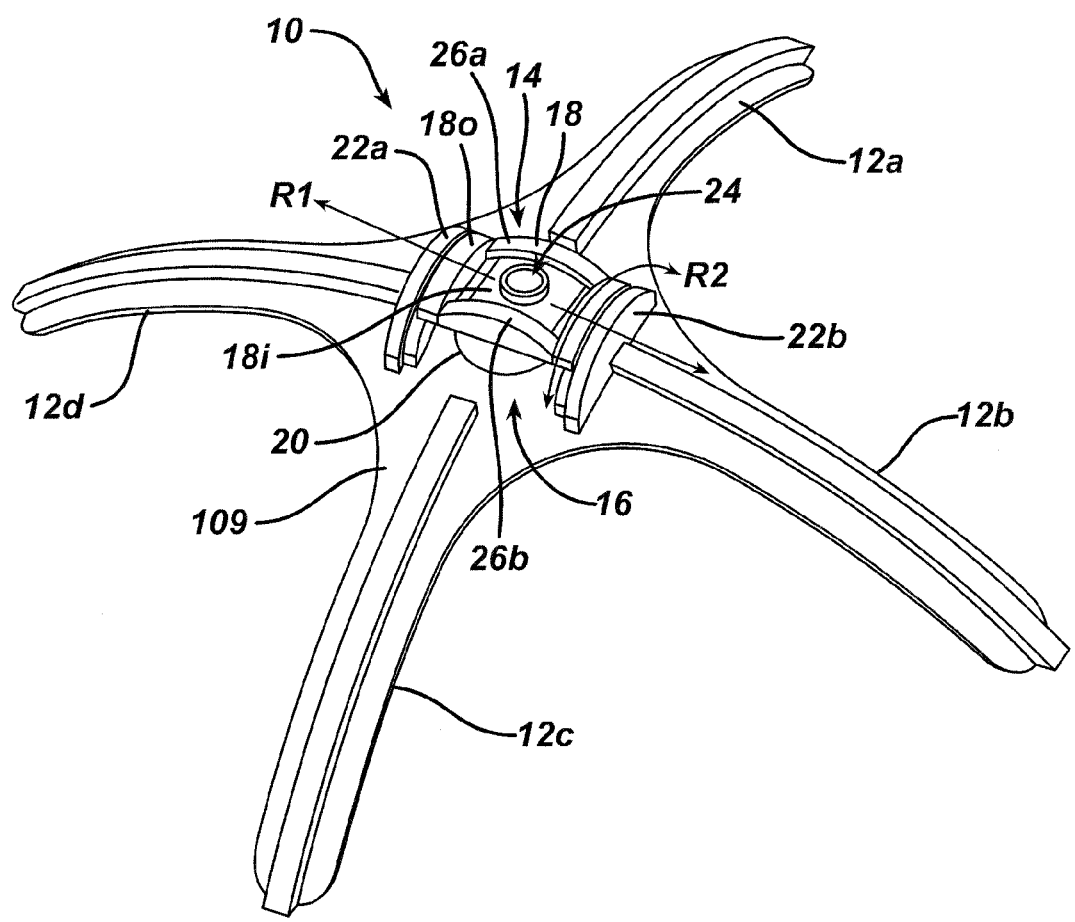
FIG. 1 is a perspective view of one embodiment of a surgical support system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary devices and methods are provided for performing minimally invasive surgical procedures. In general, the devices and methods allow a surgical instrument to be supported by a surgical support system configured to controllably guide the instrument to a desired position at surgical site. In an exemplary embodiment, a surgical support system includes a guide port defining a pivot point about which a surgical instrument advanced therethrough can pivot. The guide port, and hence the pivot point, can be located a distance above or remote from a tissue surface through which the instrument is advanced.

In another general aspect, the methods and devices allow for expansion of a volume of, e.g., insufflation of, a body cavity without introduction of an insufflation fluid therein. In an exemplary embodiment, a mechanical insufflation device can include a distal member having a plurality of expandable arms. The arms can be configured to selectively expand and unexpand to mechanically insufflate a body cavity. When expanded, the arms can push or retract adjacent tissue and define a working space at a surgical site. The mechanical insufflation device can optionally be used with the surgical support system.

A person skilled in the art will appreciate that while the methods and devices are described in connection with laparoscopic procedures in which one or more surgical instruments are inserted into a patient's body through an artificial opening, e.g., an incision, the methods and devices disclosed herein can be used in numerous surgical procedures and with numerous surgical instruments. By way of non-limiting example, the methods and devices can be used in open surgical procedures.

A person skilled in the art will also appreciate that the devices disclosed herein can be inserted into a body in any way, such as through a natural orifice, through an incision or puncture hole formed in tissue, etc. The devices can be inserted directly into a patient's body or can be inserted through an access device having a working channel through which a shaft of a surgical instrument can be advanced. A person skilled in the art will further appreciate that an access device can be configured to allow insertion of a single surgical instrument therethrough, such as with a straight cannula, or to allow simultaneous insertion of multiple instruments therethrough, such as with a surgical access device having multiple sealing ports each defining a working channel. Devices disclosed herein can alternatively or additionally be introduced into a body through an auxiliary passageway along the outside of a scoping device or other surgical instrument, as will be appreciated by a person skilled in the art. Exemplary embodiments of a surgical instrument that provides such an auxiliary passageway are described in more detail in U.S. Pat. No. 7,615,005 issued Nov. 10, 2009 entitled "Medical Apparatus For Use With An Endoscope," which is hereby incorporated by reference in its entirety.

A patient can be prepared for a surgical procedure in any way, as will be appreciated by a person skilled in the art. For example, the patient can be fully sedated or consciously sedated for the procedure. Non-limiting embodiments of a conscious sedation system can be found in U.S. Patent Publication No. 2006/0042636 filed on Jun. 21, 2005 and entitled "Oral Nasal Cannula," U.S. Pat. No. 6,807,965 issued Oct. 26, 2004 and entitled "Apparatus And Method For Providing A Conscious Patient Relief From Pain And Anxiety Associated With Medical Or Surgical Procedures," U.S. Pat. No. 7,201,734 issued Apr. 10, 2007 and entitled "Apparatus For Drug Delivery In Association With Medical Or Surgical Procedures," U.S. Pat. No. 7,247,154 issued Jul. 24, 2007 and entitled "Method For Drug Delivery In Association With Medical Or Surgical Procedures," which are hereby incorporated by reference in their entireties.

As mentioned above, in some surgical procedures, a surgical support system, also referred to herein as a "support," can be used. Generally, a surgical support system can be configured so that at least a part of the surgical support system abuts or rests on a tissue surface, e.g., an external skin surface, such that an instrument guide port, generally referred to herein as a "guide port," formed in the surgical support system can be positioned a distance remote from, above, or proximal to the tissue surface. The guide port can generally include an opening that defines a pivot point such that a surgical instrument inserted through the guide port can pivot about the pivot point. In this way, the instrument can be pivoted about the pivot point to a desired location or trajectory and be controllably guided in a distal direction to and through the tissue surface. The support can therefore ease insertion of a surgical instrument into a patient's body at a precise location, e.g., through a particular incision or opening such as at the umbilicus. Similarly, the support can help guide a surgical instrument to a precise location within a patient's body, e.g., to be positioned adjacent to a target tissue, to be positioned in a cooperative relationship with another surgical instrument, etc.

The guide port can be configured to allow one or more surgical instruments to be simultaneously inserted therethrough, e.g., an endoscope having another surgical instrument advanced through a working channel thereof. In an exemplary embodiment, as discussed further below, a mechanical insufflation device can be guided through the guide port of the support. Although, as will be appreciated by a person skilled in the art, any surgical instrument can be guided through the guide port of the support, e.g., a grasper, a dissector, scissors, a knife, a retractor, an endoscope, etc.

The surgical support system can also generally be configured to lock or hold an surgical instrument inserted through the guide port in a fixed position relative to the support, thereby allowing the instrument to be locked or held in a fixed position relative to the tissue through which it is inserted. In this way, the instrument can be selectively pivoted about the pivot point to allow positioning of the instrument, e.g., a distal end thereof, within a body cavity at a substantially fixed location. Further, the instrument can be locked or held handsfree at the substantially fixed location, e.g., with the support rather than a medical professional holding the instrument while it is in use during a surgical procedure. In this way, the surgical support system can allow a surgical instrument to not be continuously hand-held and manipulated by a medical professional during a surgical procedure. Further, because a medical professional can typically only hold and manipulate one instrument per hand, which can require multiple medical professionals to be present around a patient during a surgical procedure if more than two instruments are needed in the surgical procedure, holding a surgical instrument hands-free at a surgical site can reduce crowding around the surgical space and/or can reduce a number of medical professionals needed in an operating room. Hands-free holding of an instrument can also alleviate difficulties in hand-holding a surgical instrument in a steady or static position relative to a surgical site and/or other surgical instruments, which can, in some surgical procedures, be desirable for multiple continuous minutes.

In use, as discussed further below, the surgical support system can be positioned on a tissue surface overlying a body cavity, and a surgical instrument can be advanced through the guide port such that a shaft of the surgical instrument extends through the guide port and through an opening formed in the tissue surface such that a distal end of the surgical instrument can be positioned within the body cavity. The opening can be pre-formed, e.g., using a knife or other cutting instrument, or the surgical instrument can be configured to form the opening as it advances through the tissue, e.g., using a sharp tip located at a distal end of the instrument. The support can be configured to allow the surgical instrument to pivot about the pivot point defined by the guide port before and/or after the surgical instrument's distal end is positioned within the body cavity. In this way, a trajectory of the surgical instrument's advancement from the guide port toward the tissue surface can be adjusted before the surgical instrument passes through the tissue surface by pivoting the instrument about the pivot point, and/or the surgical instrument's distal end can be moved within the body cavity by pivoting the instrument about the pivot point.

Figure 2:
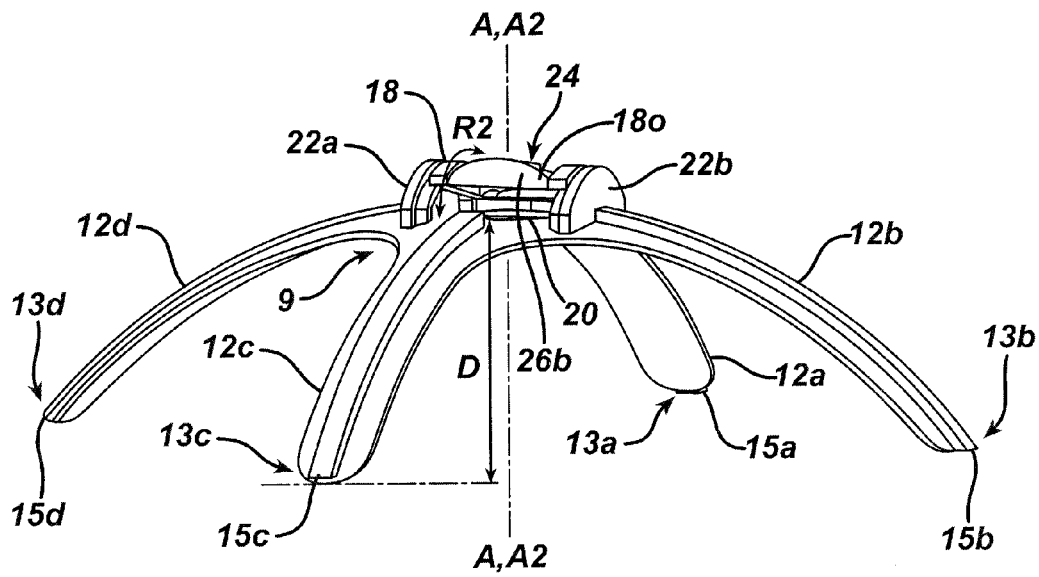
FIG. 2 is a side view of the surgical support system of FIG. 1.

In an exemplary embodiment, shown in FIGS. 1 and 2, a surgical support system 10 is provided having a plurality of legs 12a, 12b, 12c, 12d extending radially outward from a central portion 14 of the support 10, the central portion 14 defining a central longitudinal axis A of the support 10. Generally, the support 10 can be configured to help guide a surgical instrument to a surgical site and hold the surgical instrument in a desired position relative to the surgical site. As in the illustrated embodiment, the support 10 can be configured to be positioned entirely remote from, above, or proximal to the tissue surface such that the support 10 does not penetrate or enter the patient's body. Alternatively, a portion of the support 10 can be configured to penetrate or enter the patient's body, such as to help secure the support 10 to the patient with one or more of the legs 12a, 12b, 12c, 12d having penetrating distal tips, as discussed further below. Together, the legs 12a, 12b, 12c, 12d and the central portion 14 can define a base 9 of the support 10.

The support 10 can be made from any one or combination of rigid and/or flexible materials. In an exemplary embodiment, the materials forming the support 10 are biocompatible and rigid.

The legs 12a, 12b, 12c, 12d can have a variety of sizes, shapes, and configurations. Although the support 10 includes four legs in the illustrated embodiment, the support can include any number of legs. The legs 12a, 12b, 12c, 12d can generally be configured to abut or rest upon a tissue surface, e.g., an external skin surface, of a patient such that the support 10 is positioned remote from, above, or proximal to the tissue surface. The legs 12a, 12b, 12c, 12d can be such that the central portion 14 is raised or a distance D remote from, above, or proximal to distal tips 13a, 13b, 13c, 13d of the legs 12a, 12b, 12c, 12d. As in the illustrated embodiment, the legs 12a, 12b, 12c, 12d can each have a same size and shape and be angled from a plane of the central portion 14 by having an arcuate shape such that the base 9 forms a dome shape, although the legs 12a, 12b, 12c, 12d can angle in other ways, e.g., extend linearly in a distal direction from the central portion to form a pyramid shape. One or more of the legs 12a, 12b, 12c, 12d can include a protrusion 15a, 15b, 15c, 15d formed on their respective distal tips 13a, 13b, 13c, 13d. The protrusions 15a, 15b, 15c, 15d can be configured to provide a substantially flat surface configured to abut or rest on a tissue surface without penetrating into the tissue, which can help reduce injury or irritation to a patient.

One or more of the legs 12a, 12b, 12c, 12d can optionally include a fastener mechanism configured to facilitate securing the support 10 to a patient to help reduce slippage of the support 10 relative to the patient when the support 10 abuts the patient's tissue during surgery. The fastener mechanism can have a variety of configurations. For non-limiting example, the fastener mechanism can include an adhesive configured to temporarily adhere to skin, a textured surface, or other gripping material on one or more of the legs 12a, 12b, 12c, 12d, e.g., on a distal surface of the tips 13a, 13b, 13c, 13d. For another non-limiting example, the fastener mechanism can include one or more straps coupled to one or more of the legs 12a, 12b, 12c, 12d, e.g., fabric ties, VELCRO® strips, etc., configured to strap to one another, to a surgical drape, to a surgical table, or to another structure to help secure the support 10 in place relative to the patient.

The central portion 14 can include a non-movable lower or distal portion 16 and a movable upper or proximal portion 18 configured to be relative to a remainder of the support 10. The non-movable portion 16 can generally include the base 9 and can include a central hole or bore 20, generally referred to herein as a "bore," from which the legs 12a, 12b, 12c, 12d radially extend outward. The bore 20 can thus be above or proximal to the tips 13a, 13b, 13c, 13d of the legs 12a, 12b, 12c, 12d by the distance D. The bore 20 in the illustrated embodiment has a circular shape, but the bore can have any shape, as well as any size. Also as in the illustrated embodiment, the bore 20 can be central to the support 10 such that the central longitudinal axis A can pass through a center point of the bore 20 such that the support 10 and the bore 20 have a common central longitudinal axis.

The non-movable portion 16 can also include at least one support guide or rail 22a, 22b, generally referred to herein as a "rail," configured to secure the movable portion 18 to a remainder of the support 10, e.g., to the non-movable portion 16 and to the legs 12a, 12b, 12c, 12d, while allowing guided movement of the movable portion 18 relative to the remainder of the support 10. The illustrated support embodiment includes two arcuate rails 22a, 22b, but the support can include any number of rails having any shape.

The movable portion 18 can include an instrument guide port 24, generally referred to herein as a "guide port," formed therein. Generally, the guide port 24 can be located in the central portion 14 and can define an opening configured to receive a surgical instrument therethrough. The guide port 24 can have any size and shape. In the illustrated embodiment, the guide port 24 has a cylindrical shape, thereby allowing a surgical instrument having a cylindrical elongate shaft to be smoothly and controllably advanced therethrough. The guide port 24 can have any diameter to accommodate any size instrument. In an exemplary embodiment, the guide port 24 can have a diameter slightly larger than a traditional endoscopic instrument shaft diameter, e.g., slightly larger than 10 mm, slightly larger than 7 mm, slightly larger than 15 mm, etc. In some embodiments, the guide port 24 can be divided into channels, e.g., four quadrants, to facilitate advancement of multiple instruments therethrough. The movable portion 18 can include any number of guide ports, such as a plurality of guide ports of different shapes and/or sizes to accommodate instruments of various shapes and sizes.

The guide port 24 can optionally include at least one sealing element positioned therein. Various sealing elements are known in the art, such as an instrument seal that forms a seal around an instrument disposed therethrough, but otherwise does not form a seal when no instrument is disposed therethrough, a channel seal or zero-closure seal that seals the working channel created by the sealing port when no instrument is disposed therethrough, or a combination instrument seal and channel seal that is effective to both form a seal around an instrument disposed therethrough and to form a seal in the working channel when no instrument is disposed therethrough.

Figure 3:
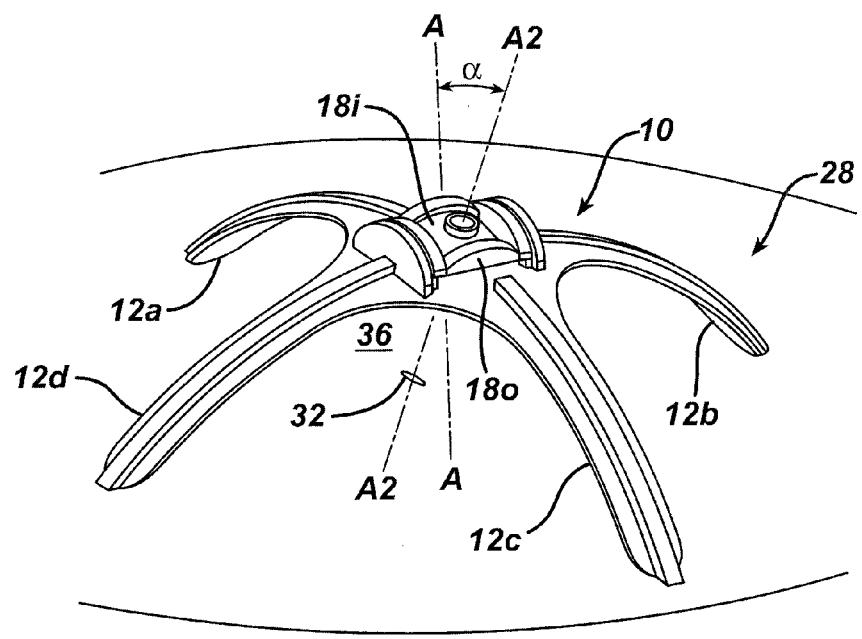
FIG. 3 is a perspective view of the surgical support system of FIG. 1 positioned on an exterior skin surface.
Figure 4:
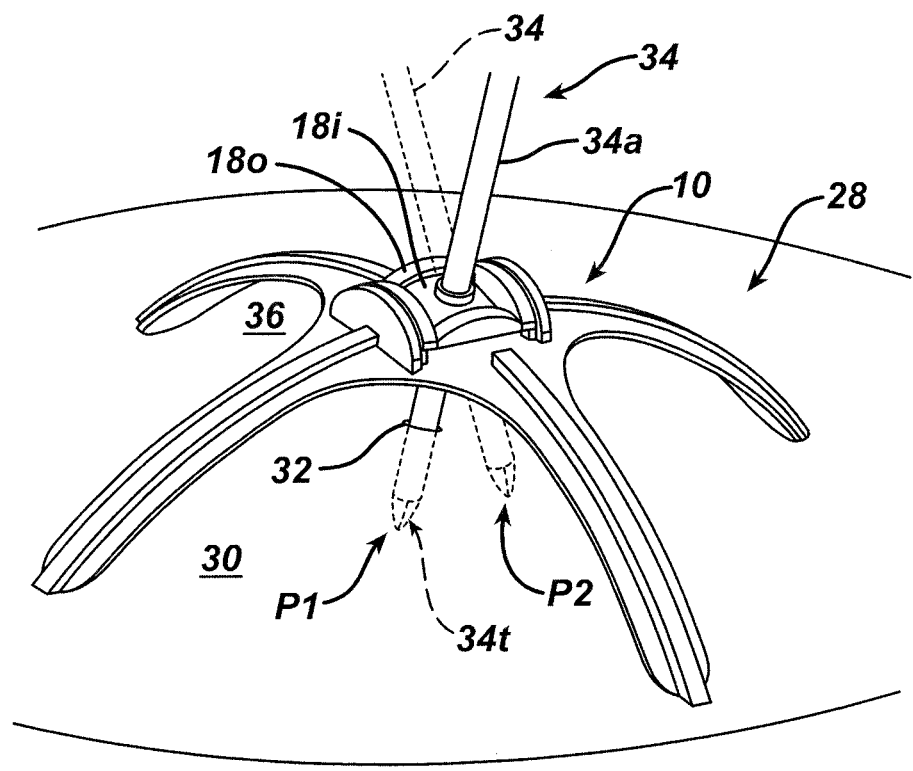
FIG. 4 is a perspective, partially transparent view of the surgical support system of FIG. 4 having a surgical instrument advanced therethrough, a distal end of the surgical instrument being positioned within a body cavity underlying the exterior skin surface.

The guide port 24 can have a cooperative relationship with the bore 20 such that regardless of the position of the movable portion 18 relative to a remainder of the support 10, a central longitudinal axis A2 of the guide port 24 can pass through the bore 20. In this way, an instrument advanced through the guide port 24 along the guide port's longitudinal axis A2 can advance through the bore 20 to a location distally beyond the support 10, as discussed further below. In FIGS. 1 and 2, the longitudinal axes A, A2 are the same, e.g., not angularly oriented relative to one another, but as discussed further below and as illustrated in FIGS. 3 and 4, the movable portion 18 can be moved to a position relative to a remainder of the support 10 such that the guide port's axis A2 can be angularly oriented from the bore's axis A at an angle α.

The movable portion 18 can be configured to be movable in at least one plane of motion or one dimension, e.g., movable in an x dimension, movable in a y dimension, movable in a z dimension, or any combination thereof. In this way, the guide port 24 formed in the movable portion 18 can be movable in at least one plane of motion or one dimension to selectively position the guide port 24 relative to a tissue surface upon which the support 10 rests and/or relative to a body cavity underlying the tissue surface, thereby allowing an instrument advanced through the guide port 24 to be predictably and controllably advanced to the tissue surface and/or the body cavity. In the illustrated embodiment, the movable portion 18 is movable in three planes of motion or three dimensions. As in the illustrated embodiment, the movable portion 18 can be movable in first and second directions to accomplish three dimensional movement. Movement of the movable portion 18 in the first direction, shown by double-sided arrow R1 in FIG. 1, can move the guide port 24 in, e.g., the y dimension. Movement of the movable portion 18 in the second direction, shown by double-sided arrow R2 in FIGS. 1 and 2, can move the guide port 24 in, e.g., the x and z dimensions. A person skilled in the art will appreciate that a double-sided arrow such as the arrows R1, R2 indicates possible movement in both directions indicated by the arrows at either end of the double-sided arrow.

The movable portion 18 can, as in the illustrated embodiment, include inner and outer portions 18i, 18o. The inner portion 18*i* is shaded for clarity in FIG. 1. The inner and outer portions 18*i*, 18*o* can each be movable relative to a remainder of the support 10. The outer portion 18*o* can be movably coupled to and extend between the rails 22*a*, 22*b* such that the outer portion 18*o* can move in an arc, e.g., in the second direction shown by arrow R2, to selectively position the guide port 24 in the x and z dimensions. The inner portion 18*i* can be movably coupled to and extend between rails 26*a*, 26*b* of the outer portion 18*o* such that the inner portion 18*i* can move, e.g., slide, in a linear direction, e.g., in the first direction shown by arrow R1, to selectively position the guide port 24 in the y dimension. As mentioned above, the movable portion 18 can be configured to engage the rails 22*a*, 22*b* and move, e.g., slide, relative thereto to facilitate selective positioning of the movable portion 18. The inner portion 18*i* can therefore be slidably movable along the rails 26*a*, 26*b* in the first direction relative to the outer portion 18*o*, while slidable movement of the outer portion 18*o* along the rails 22*a*, 22*b* in the second direction can also move the inner portion 18*i* relative to the rails 22*a*, 22*b* in the second direction.

The movable portion 18, and hence the guide port 24, can be configured to be selectively locked in a fixed position relative to a remainder of the support 10, such as when the guide port's longitudinal axis A2 has been angularly oriented at a desired angle α from the bore's axis A. Any lock mechanism can be used to lock the movable portion 18, as will be appreciated by a person skilled in the art. For non-limiting example, the movable portion 18 can include at least one squeeze and release tab having a released position in which the movable portion 18 is configured to slide relative to a remainder of the support 10, and an unreleased position in which the movable portion cannot slide relative to a remainder of the support 10. The movable portion 18 can include one lock mechanism, or it can include a first lock mechanism for the outer portion 18*o* and a second lock mechanism for the inner portion 18*i*. Having two lock mechanisms can help facilitate precise positioning of the movable portion 18, e.g., by allowing the inner portion 18*i* to first be selectively positioned and locked in the y dimension and then allowing the outer portion 18*o* to be selectively positioned and locked in the x and z dimensions.

In use, one or more surgical instruments can be inserted into a body cavity through the support 10, which can help optimally position the surgical instruments relative to the body cavity through movement of the movable portion 18. As illustrated in FIG. 3, the support 10 can be placed upon an exterior skin surface 28 with the tips 13*a*, 13*b*, 13*c*, 13*d* of the legs 12*a*, 12*b*, 12*c*, 12*d* resting upon the exterior skin surface 28. The exterior skin surface 28 can be any tissue surface, but in the illustrated embodiment, it is an abdomen overlying an abdominal cavity 30, shown in FIG. 4. Each of the legs 12*a*, 12*b*, 12*c*, 12*d* can abut the exterior skin surface 28, but in some circumstances, each of the legs 12*a*, 12*b*, 12*c*, 12*d* may not directly contact the exterior skin surface 28 when the support 10 is in its intended surgical position, e.g., if the patient's skin surface is uneven, if a surgical drape covers a portion of a patient where a support leg rests, etc.

Either before or after the support 10 is positioned on the exterior skin surface 28, an incision 32 can be formed in the exterior skin surface 28 through which an instrument can be advanced. A person skilled in the art will appreciate that the incision 32 can pierce through the exterior skin surface 28 to the cavity 30 or that the incision 32 can penetrate only partially through the skin such that an instrument can be inserted into the partial incision 32 and finish penetrating through the skin to the cavity 30. A person skilled in the art will also appreciate that, as mentioned above, the incision 32 can be pre-formed or that a surgical instrument advancing to the cavity 30 can be configured to form the incision 32 as it advances through the surface 28 and into the cavity 30, such as with a distal end of the instrument.

Regardless of how the incision 32 is formed, a surgical instrument 34 can be advanced through a proximal end of the guide port 24, through the bore 20, and into open dome-shaped space 36 defined by the legs 12*a*, 12*b*, 12*c*, 12*d* and located between a distal end of the guide port 24 and the exterior skin surface 28. Although the instrument 34 in the illustrated embodiment is a grasper having opposed movable jaws at its distal tip 34*t*, any instrument can be inserted through the port 24 of the support 10. Although not illustrated, the instrument 34 can have a handle at its proximal end to facilitate handling of the instrument 34. An elongate member or shaft 34*a* of the instrument 34 can thus be slidably received within the guide port 24, with a proximal portion of the instrument 34 located proximal to the guide port 24, and with a distal portion of the instrument 34 located within the open dome-shaped space 36. The instrument 34 can continue to be advanced through the guide port 24 to pass the instrument's distal portion from within the open dome-shaped space 36, through the incision 32, and into the cavity 30, as shown in FIG. 4. Any amount of the instrument 34 can be positioned within the cavity 30. With the instrument's distal portion located within the cavity 30, the instrument 34 can be used in a surgical procedure within the cavity 30, e.g., by grasping tissue with its distal tip 34*t*.

Before and/or after the instrument 34 is received within the guide port 24, as well as before and/or after the instrument's distal portion is located within the cavity 30, the movable member 18, e.g., the inner and/or outer portions 18*i*, 18*o*, can be selectively moved to position the guide port 24 at a selected location relative to a remainder of the support 10, to the skin surface 28, and to the underlying body cavity 30. Although the movable portion 18 can be configured to be movable relative to a remainder of the support 10 with or without an instrument inserted through the guide port 24, e.g., by being manually moved by hand, the movable portion 18 can also be configured to move relative a remainder of the support 10 in response to motion of at least one instrument inserted through the guide port 24. The support 10 can remain in contact with the skin surface 28 when the movable portion 18 moves. The guide port's axis A2 can therefore be angularly offset at the angle α from the bore's axis A, as shown in FIG. 3, to facilitate advancement of the instrument 34 through the incision 32 and/or to a desired location within the cavity 30. For non-limiting example, with the guide port 24 in a first position relative to a remainder of the support 10, the instrument's distal tip 34*t* can be positioned at a first position P1 within the cavity 30. The guide port 24 can then be moved to a second, different position relative to a remainder of the support 10, by hand or by movement of the instrument 34, to move from the instrument's distal tip 34*t* from the first position P1 to a second, different position P2 within the cavity 30. The second position P2 can, as discussed above, be different from the first position P1 in the x dimension, y dimension, z dimension, or any combination thereof. In the embodiment illustrated in FIG. 4, the second position P2 varies from the first position P1 in three dimensions. The instrument's distal tip 34*t* can be moved to any number of positions within the cavity 30 any number of times. By providing the guide port 24 and hence the pivot point defined by the guide port 24, at the distance D remote from, above, or proximal to the skin surface 28, the instrument 34 can have a greater range of motion than if the pivot point was located substantially at the skin surface 28.

The guide port 24 can also be configured to allow rotational movement of the instrument 34 about the guide port's longitudinal axis A2 when the instrument 34 is received within the guide port 24. Such rotational movement can help optimally position a distal portion of the instrument 34 within the cavity 30.

Figure 5:
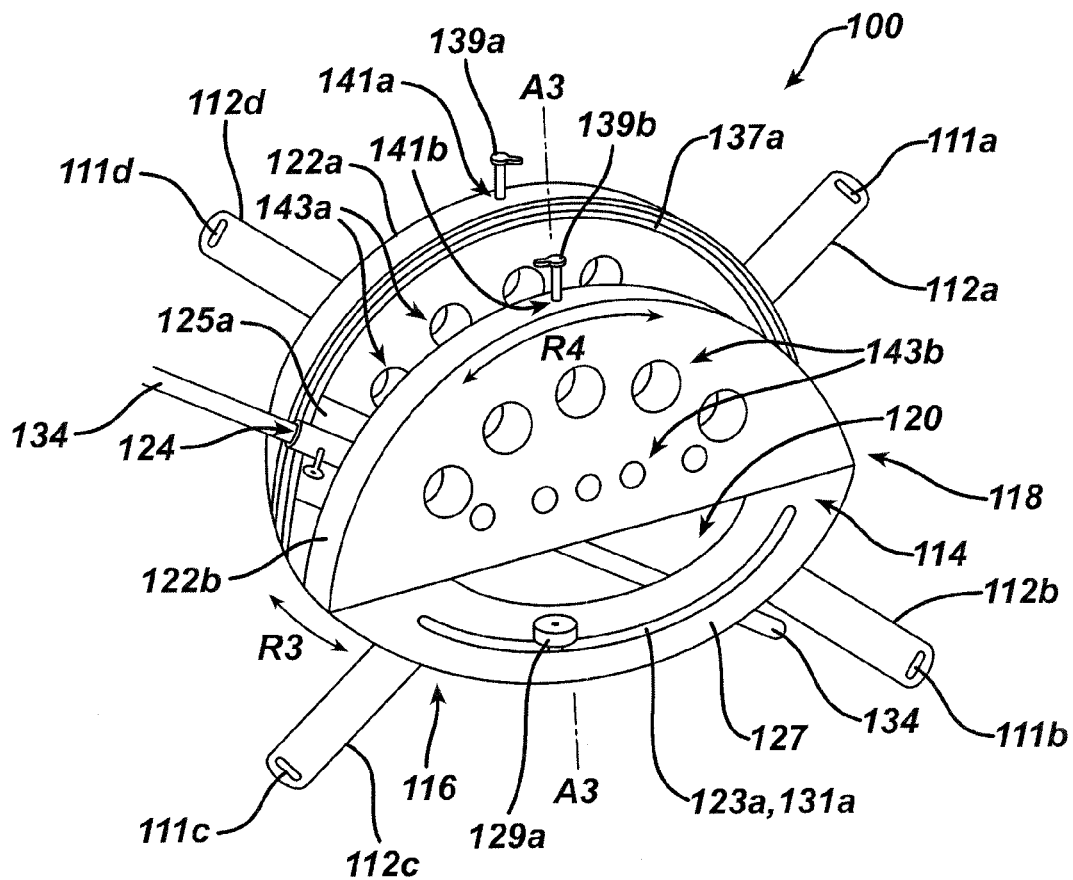
FIG. 5 is a perspective view of another embodiment of a surgical support system.
Figure 6:
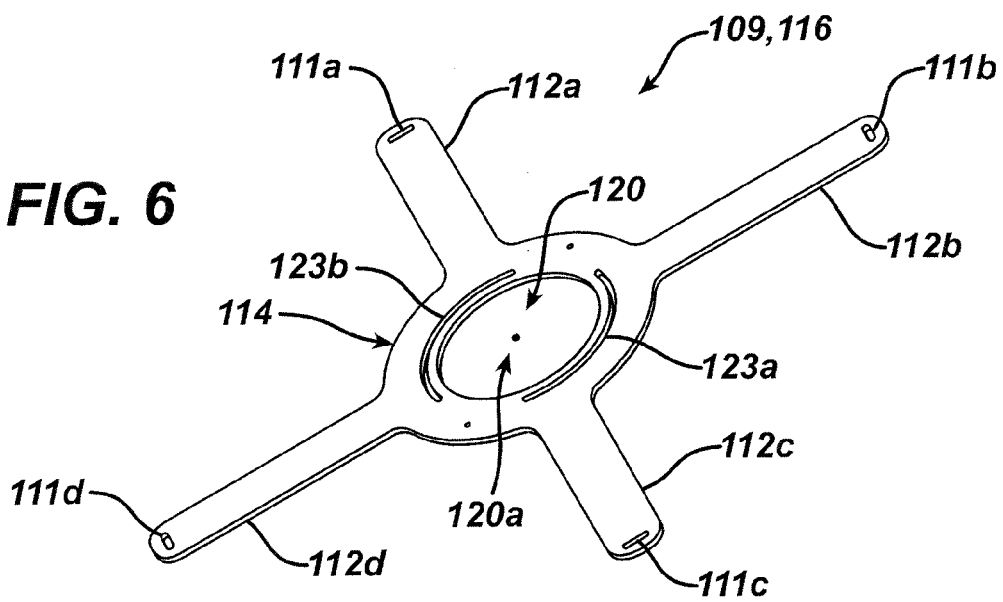
FIG. 6 is a perspective view of a base of the surgical support system of FIG. 5.

FIG. 5 illustrates another exemplary embodiment of a surgical support system 100. FIGS. 6-9 illustrate various elements of the support 100, discussed further below. The support 100 can generally be configured and used similar to the surgical support system 10 of FIGS. 1-4. The support 100 includes a plurality of legs 112a, 112b, 112c, 112d extending radially outward from a central portion 114 of the support 100, the central portion 114 defining a central longitudinal axis A3 of the support 10. Together, the legs 112a, 112b, 112c, 112d and the central portion 114 can define a base 109 of the support 100, shown in FIG. 6.

As discussed above regarding the legs 12a, 12b, 12c, 12d of the support 10, the legs 112a, 112b, 112c, 112d can have a variety of sizes, shapes, and sizes. In this illustrated embodiment, the legs 112a, 112b, 112c, 112d each have a same size and shape, are linear, and extend radially outward in a same plane as the central portion 114. In other words, the base 109 can be substantially flat such that the legs 112a, 112b, 112c, 112d can be configured to allow an entirety of their distal surfaces to abut or rest against an exterior tissue surface. Allowing the distal surfaces to completely, directly contact the exterior tissue surface can help stabilize the support on the exterior tissue surface and help prevent the support 100 from slipping relative thereto. Although, similar to that discussed above, all or a portion of any one or more of the legs 112a, 112b, 112c, 112d may not directly contact an exterior skin surface when the support 100 is in its intended surgical position on a patient, which can be with at least two of the legs 112a, 112b, 112c, 112d in direct contact with the patient's skin to stabilize the support 100 thereon. Each of the legs 112a, 112b, 112c, 112d includes a hole or window 111a, 111b, 111c, 111d configured to couple to a fastener mechanism such as one or more straps. The holes or windows 111a, 111b, 111c, 111d are formed at the legs' outward ends, but they can be located anywhere in the legs 112a, 112b, 112c, 112d or elsewhere in the support 100. In an exemplary embodiment, a proximal surface of each of the legs 112a, 112b, 112c, 112d can have one side of VELCRO® strip adhered or otherwise secured thereto such that a complementary side of a VELCRO® strip attached to a surgical table or other stable structure can be fed through the holes or windows 111a, 111b, 111c, 111d and releasably stuck to the proximal leg surface VELCRO® strip to hold the support 100 in place.

The central portion 114 can include a non-movable lower or distal portion 116 that includes the base 109, and a movable upper or proximal portion 118 configured to be movable relative to a remainder of the support 100. The non-movable portion 116 can define a central bore 120 such that the legs 112a, 112b, 112c, 112d can radially extend outward from a ring-shape. The central longitudinal axis A3 can pass through a center point 120a of the bore 120 such that the support 100 and the bore 120 have a common central longitudinal axis, e.g., the axis A3, and such that a plane of the base 109 is substantially perpendicular to the support's axis A3.

The non-movable portion 116 can also include at least one track, groove, or channel 123a, 123b, generally referred to herein as a "track," configured to movably engage the movable portion 118. The support 100 includes two tracks 123a, 123b, but the support 100 can include any number of tracks. The tracks 123a, 123b in the illustrated embodiment are arcs partially outlining the bore 120, but the tracks 123a, 123b can have any shape.

The movable portion 118 can include a guide port 124, similar to the guide port 24 of the FIG. 1 support embodiment, and be configured to receive a surgical instrument therein and to be in a cooperative relationship with the bore 120. Similar to the movable portion 18 of the FIG. 1 support embodiment, the movable portion 118 of the support 100 can be configured to be movable in at least one plane of motion or one dimension. The movable portion 118 can also similarly include inner and outer portions that can each be movable relative to a remainder of the support 100.

Figure 7:
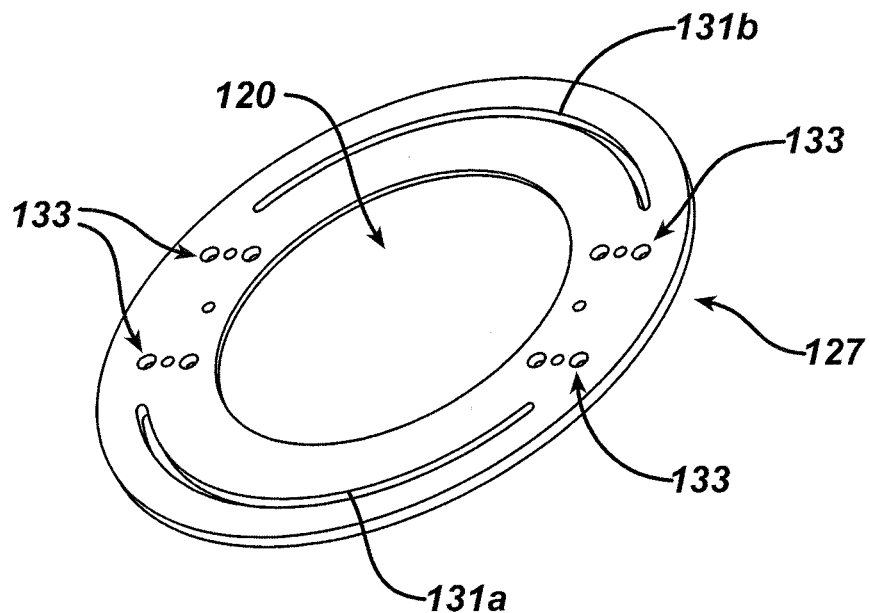
FIG. 7 is a perspective view of a rim of the surgical support system of FIG. 5.
Figure 8:
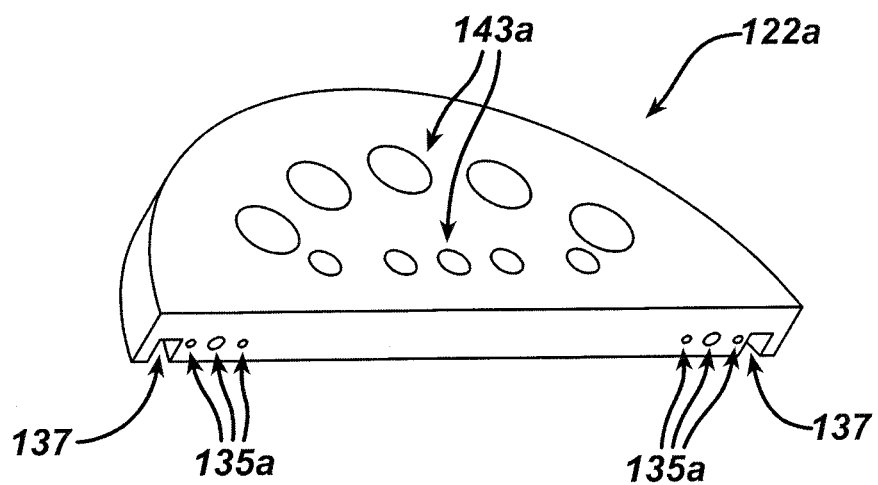
FIG. 8 is a perspective view of a rail of the surgical support system of FIG. 5.
Figure 9:
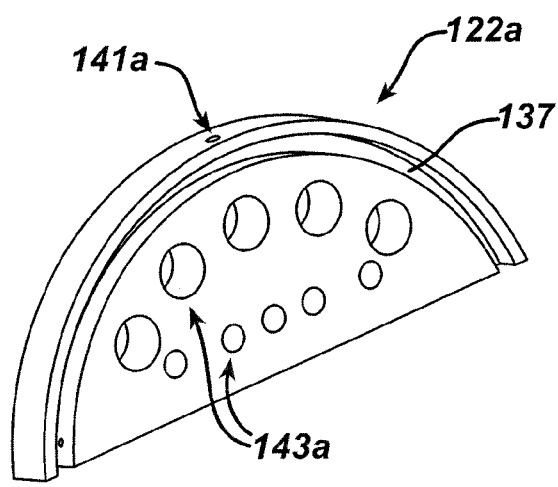
FIG. 9 is another perspective view of the rail of the surgical support system of FIG. 5.

The outer portion of the movable portion 118 can include a rim 127 configured to be movably coupled to the base 109 such that a distal surface of the rim 127 faces a proximal surface of the base 109. The rim 127 can also be in a cooperative relationship with the base 109 to define the bore 120. The rim 127 can be configured to be selectively moved relative to the base 109, such as by being rotatable about the central axis A3, as shown by double-sided arrow R3 in FIG. 5. The rim 127 can include tracks 131a, 131b configured to align with the tracks 123a, 123b of the base 109 such that a thumbscrew 129a positioned in each of the tracks 123a, 123b, 131a, 131b can be selectively loosened, to allow movement of the rim 127 relative to the base 109, and tightened, to lock the rim 127 in a fixed position relative to the base 109. The thumbscrew positioned in the tracks 123b, 131b is obscured from view in FIG. 5. A person skilled in the art will appreciate that the thumbscrew 129a or any other lock mechanism can be used to lock the relative positions of the rim 127 and the base 109, e.g., a clamp, corresponding holes and depressible pins, etc. As shown in FIG. 7, the rim 127 can also include a plurality of through holes 133 configured to engage and secure the rails 122a, 122b thereto, e.g., with pegs (not shown) configured to fit into the through holes 133 and corresponding through holes formed in a distal surface of the rails 123a, 123b. FIG. 8 illustrates through holes 135a formed in the rail 123a, but a person skilled in the art will appreciate that the other rail 123b can include similar through holes and otherwise be configured similar to the rail 123a illustrated in FIGS. 8 and 9.

The inner portion of the movable portion 118 can include at least one rail 122a, 122b movably coupled to the rim 127, at least one guide port holder movably coupled to corresponding one of the rails 122a, 122b, and the guide port 124. A guide port holder 125a coupled to the rail 122a is visible in FIG. 5, but the other rail 122b also has a guide port holder coupled thereto which is obscured from view. The guide port 124 can be coupled to facing sides of the guide port holders coupled to the rails 122a, 122b, thereby extending between the guide port holders and being positioned between the rails 122a, 122b. The illustrated support embodiment includes two arcuate rails 122a, 122b, but the support can include any number of rails having any shape. The guide port holders can be configured to engage the rails 122a, 122b, e.g., in tracks 137a formed therein (tracks in the other rail 122b are obscured in FIG. 5), and move, e.g., slide, relative thereto in a direction shown by double-sided arrow R4 in FIG. 5, to facilitate selective positioning of the movable portion 118. The inner portion can therefore be slidably movable along the rails 122a, 122b. Thumbscrews 139a, 139b positioned in thumbscrew holes 141a, 141b formed in each of the rails 122a, 122b can be selectively loosened, to disengage from the guide holders to allow movement of the guide holders within the tracks relative to the rails 122a, 122b, and tightened, to engage, e.g., press against, and lock the guide holders in a fixed position relative to the rails 122a, 122b.

The rails 122a, 122b can optionally each include one or more portholes 143a, 143b formed in sidewalls thereof, although the portholes 143a, 143b can be formed in the sidewalls and/or any other portion of the rails 122a, 122b. The portholes 143a, 143b can be configured to ease handling of the rails 122a, 122b, e.g., by serving as grips or holds for fingers or instruments. The portholes 143a, 143b can have any size and shape, and each of the rails 122a, 122b can include any number of portholes 143a, 143b, same or different on each rail 122a, 122b.

As mentioned above, the support 100 can be used similar to the support 10 of FIG. 1. Generally, the guide port 124 can be selectively positioned relative to the base 109, to a tissue surface upon which the support 100 rests, and to a body cavity underlying the tissue surface. The guide port 124 can be selectively positioned by rotating the rim 127 relative to the base 109, which also rotates the rails 122a, 122b, and hence the guide port 124, coupled to the rim 127 in a fixed position, and/or moving the guide holders along the tracks of the rails 122a, 122b. The thumbscrews 129a, 139a, 139b (and the obscured thumbscrew positioned in the tracks 123b, 131b) can be loosened and tightened to facilitate movement and locking of the rim 127 and the guide holders, as discussed above. The presence of the thumbscrew 129a (and the obscured thumbscrew positioned in the tracks 123b, 131b) can limit rotational movement of each of the rails 122a, 122b to about 180 degrees, but in other embodiments, the rails 122a, 122b can be configured to rotate another amount, such as 360 degrees. Either before or after the guide port 124 is moved to a desired position, an instrument 134 can be advanced through the guide port 124, through the bore 120, and through the tissue surface upon which the support 100 rests. The instrument 134 in the illustrated embodiment includes a rigid cannula configured to receive one or more instruments therein, but as mentioned above, any instrument can be advanced through the guide port.

As also mentioned above, in an exemplary embodiment, a mechanical insufflation device, generally referred to herein as a "mechanical insufflator," can be advanced through a guide port of a surgical support system and locked in place therein to position and hold a distal end of the mechanical insufflation device at a selected position relative to a surgical site. However, while a mechanical insufflation device such as those discussed herein can be used with a surgical support system, a mechanical insufflation device need not be used with a surgical support system and can be introduced to a surgical site in another way, e.g., through a standard trocar, directly through an opening in tissue, etc. Generally, a mechanical insufflation device can allow a patient to be operated on without introducing an insufflation fluid into a patient to, e.g., expand a body cavity to provide adequate work space at a surgical site. Instead, a patient's body cavity can be mechanically insufflated using the device. Because insufflating a patient's body cavity using an insufflation fluid typically requires a patient to be put on a respirator and to be sedated because breathing becomes difficult or impossible while insufflated with fluid, using a mechanical insufflation device can save surgical resources and reduce risk of complications resulting from respiration and sedation.

Figure 10:
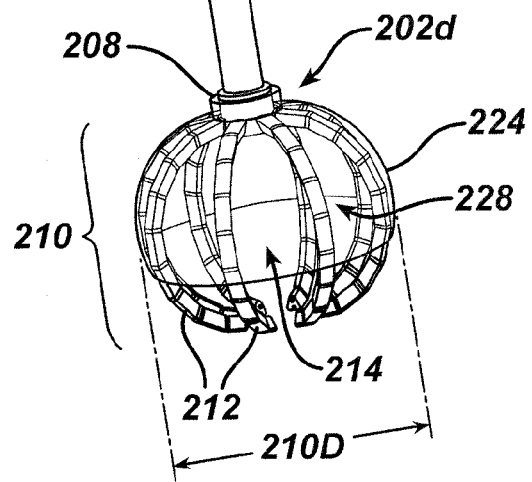
FIG. 10 is a perspective view of one embodiment of a mechanical insufflation device having a plurality of arms, the arms being in an expanded configuration.
Figure 11:
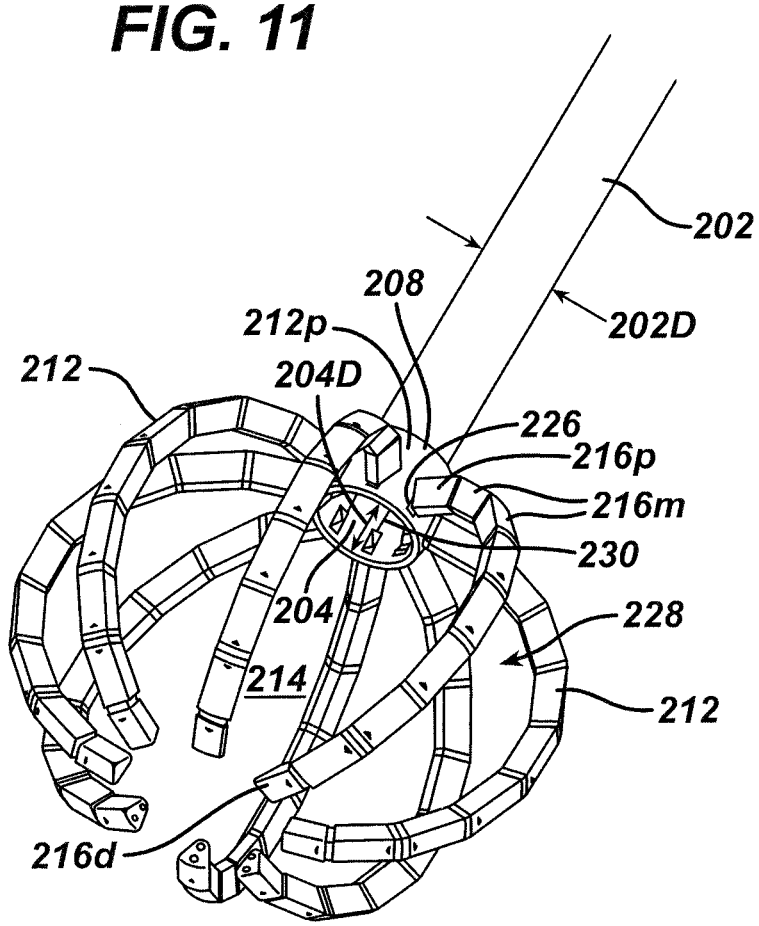
FIG. 11 is a perspective view of a distal portion of the mechanical insufflation device of FIG. 10.

FIGS. 10 and 11 illustrate an exemplary embodiment of a mechanical insufflation device 200. The mechanical insufflator 200 can generally include an elongate member or shaft 202, generally referred to herein as a "shaft," having a proximal end 202p and a distal end 202d with an inner lumen 204 extending therebetween such that the shaft 202 is cannulated. The proximal end 202p can have a handle coupled thereto to facilitate handling of the device 200, as discussed further below. The shaft 202 can optionally include at least one sealing element positioned therein.

In the illustrated embodiment, the device's proximal end 202p includes a stop member 203 configured to stop the device 200 from advancing too far in a distal direction, as also discussed further below. A hub 208 can be formed at the distal end 202d and can be configured to couple to an expander member 210 including a plurality of arms 212. The hub 208 can include a collar formed the shaft's distal end 202d, as shown in the illustrated embodiment, to which proximal ends 212p of the arms 212 can be attached, or the hub 208 can include a distal portion of the shaft 202 to which proximal ends 212p of the arms 212 can be attached to the shaft 202. The arms 212 can be positioned any distance apart from one another, same or different between various ones of the arms 212, around a circumference of the hub 208. As in the illustrated embodiment, the arms 212 can be equally spaced apart from one another around a circumference of the hub 208, and hence around the shaft 202. Such equidistant spacing can help facilitate even pushing or retracting of tissue with the arms 212.

The expander member 210 can have a variety of sizes, shapes, and configurations. Generally, the expander member 210 can be configured to move between a relaxed configuration in which the expander member 210 has a first diameter, and an enlarged configuration in which the expander member 210 has a second, larger diameter. In this way, the expander member 210 in the relaxed configuration can be advanced through a relatively small opening formed in tissue and into a body cavity and subsequently moved to the enlarged configuration. In an exemplary embodiment, as discussed further below, when the expander member 210 is positioned within a body cavity, the expander member 210 can be configured to move from the relaxed configuration to the enlarged configuration, thereby mechanically insufflating the body cavity. FIG. 10 illustrates the expander member 210 in the enlarged configuration and having an enlarged diameter 210D. The enlarged diameter 210D can have any size, e.g., in a range of about 2 to 3 inches.

As mentioned above, the expander member 210 can include a plurality of arms 212. Although the device 200 in the illustrated embodiment includes eight arms 212, the device 200 can include any number of arms. Generally, the arms 212 can each be configured to move between an unexpanded configuration in which the arm is substantially straight, and an expanded configuration in which the arm is articulated. The arms 212 shown in FIGS. 10 and 11 are illustrated in expanded configurations. When each of the arms 212 is in the unexpanded configuration, the arms 212 can be substantially parallel to one another, e.g., longitudinal axes of the arms 212 can be substantially parallel to one another, and the expander member 210 can be in the relaxed configuration. When the arms 212 are in the unexpanded configuration, e.g., the expander member 210 is in the relaxed configuration, a diameter of the expander member 210 can be equal to or less than a diameter 202D of the shaft 202, at least in a distal portion of the shaft 202, which can help ease introduction and removal of the expander member 210 into and from a patient's body. Also when the arms 212 are in the unexpanded configuration, the arms 212 can be in positions to obstruct the inner lumen 204 such that the inner lumen 204 is substantially blocked at a distal end thereof. In other words, the arms 212 in the unexpanded configuration can be in the way of and obstruct the inner lumen 204 such that an instrument cannot be advanced through the inner lumen 204 to extend distally beyond the hub 208. When the arms 212 move from the unexpanded to the expanded configuration, distal ends thereof can be configured to move radially outward from one another.

When the arms 212 are in the expanded configuration, the arms 212 can be angularly offset from one another, e.g., longitudinal axes of the arms can intersect one or more of each other, and the expander member 210 can be in the enlarged configuration. Also in the expanded configuration, the arms 212 can define a working space 214 therebetween. In the illustrated embodiment, the arms 212 are configured to articulate in a curved or arcuate shape such that working space 214 is substantially spherical, but the arms 212 can have any shape when articulated and can define a working space having any shape. For non-limiting example, the arms can articulate in a different curved or arcuate shape such that working space is substantially egg-shaped. For another non-limiting example, the arms can articulate at a non-zero discrete angle such that the working space has a substantially octagonal bipyramid shape. A diameter of the working space 214 defines the diameter 210D of the expander member 210 in the enlarged configuration. The expanded diameter 210D can be greater than the diameter 202D of the shaft 202, at least in a distal portion of the shaft 202, as well as greater than a diameter 204D of the inner lumen 204, at least at a distal end of the lumen 204. In this way, an instrument can be advanced through the inner lumen 204 and enter the working space 214 when the arms 212 are in the expanded configuration and the expander member is in the enlarged configuration, as discussed further below.

The device 200 can optionally include a flexible cover 224 disposed around the arms 212. For clarity, the flexible cover 224 is absent from FIG. 11. Generally, the flexible cover 224 can be configured to move between a relaxed configuration corresponding to the arms 212 being in the unexpanded configuration and the expander member 210 being in its relaxed configuration, and a flexed configuration corresponding to the arms 212 being in the expanded configuration and the expander member 210 being in the enlarged configuration. The flexible cover 224 can thus be configured to facilitate pushing or retracting tissue by gripping the tissue and/or reducing chances of the tissue slipping along the arms 212 when the arms 212 push or retract the tissue away from a surgical site. In other words, the flexible cover 224 can help prevent matter, e.g., fluid, tissue, instruments tips, etc., from entering and passing through void space 228 between adjacent arms 212, particularly when the arms 212 are fully articulated and the size of the void space 228 is therefore maximized and the arms 212 are pushing or retracting tissue away from the working space 214. The flexible cover 224 can extend distally from the proximal ends 212p of the arms 212 along at least a partial longitudinal length thereof, e.g., along about 75% of the longitudinal length of the arms 212 such that the expander member 210 can be about 75% covered. In this way, the flexible cover 224 can be configured to help protect the arms 212 and help prevent the arms 212 from snagging on or damaging tissue or other matter. The flexible cover 224 can be made from any one or more flexible materials, e.g., a surgically safe fabric such as gauze, an elastomer such as rubber, etc., configured to allow the flexible cover 224 to move when the arms 212 articulate and straighten. The flexible cover 224 can be sticky, such as with a cover formed of gauze or with a cover having a mild adhesive applied to at least an exterior surface thereof, which can help grip tissue. The flexible cover 224 can be configured as a porous netting, e.g., with a gauze, such that fluid can pass therethrough while substantially preventing passage of solid matter such as tissue therethrough.

Figure 12:
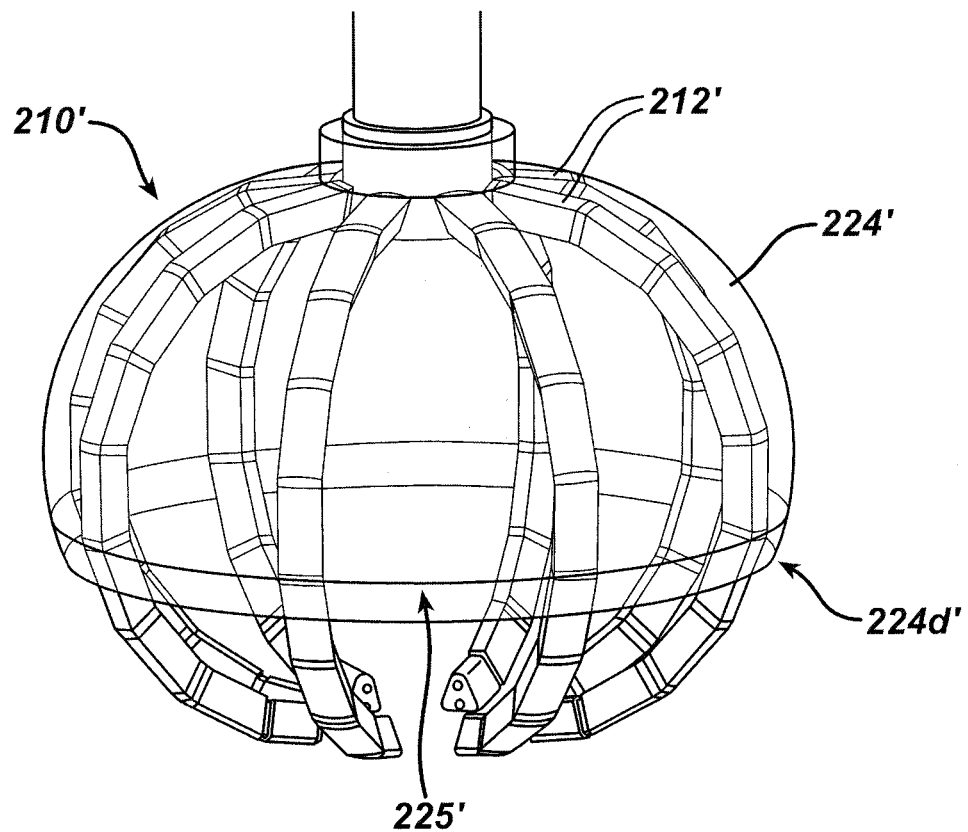
FIG. 12 is a side view of a distal portion of another embodiment of a mechanical insufflation device having a plurality of arms, the arms being in an expanded configuration.

A flexible cover disposed over arms of an expander member can optionally include a distal band or retainer, generally referred to as a "distal retainer," configured to help prevent the flexible cover from slipping a significant distance, if at all, in a proximal direction. FIG. 12 illustrates an exemplary embodiment of an expander member 210' including a plurality of arms 212' having a flexible cover 224' disposed therearound, with the flexible cover 224' including a distal retainer 225'. The expander member 210', the arms 212', and the flexible cover 224' can generally be configured and used similar to like-named elements of FIGS. 10 and 11. The distal retainer 225' can have a variety of sizes, shapes, and configurations. Generally, the distal retainer 225' can include a closed-loop or circumferential flexible member configured to move with the flexible cover 224' and help retain the arms 212' in an unexpanded configuration, which can help facilitate insertion of the arms 212' into a patient. The distal retainer 225' has a circular ring shape in the illustrated embodiment, but it can have any shape. The distal retainer 225' can be formed of any one or more flexible materials, such as an elastic. The distal retainer 225' can be attached to the flexible cover 224' in any way, such as by being integrally formed with the flexible cover 224' or being attached to an interior or exterior surface thereof using an adhesive, heat molding, or in any other way, as will be appreciated by a person skilled in the art. The distal retainer 225' can be located a relatively small distance proximally from a distal-most end 224d' of the distal retainer 224', as in the illustrated embodiment, or be located at the distal-most end 224d'. Having the distal retainer 225' at or near the distal-most end 224d' can help maximize retention of the arms 212' and help prevent curling or sliding of the flexible cover 224' at the distal end thereof.

Referring again to FIGS. 10 and 11, the arms 212 can have a variety of sizes, shapes, and configurations. In an exemplary embodiment, each of the arms 212 is identical to one another. In some embodiments, the arms can have different longitudinal lengths, which can help improve visualization proximate to shorter arms. The arms 212 can be configured to facilitate articulation thereof in any number of ways. In an exemplary embodiment, the arms can be integral members having a weakened or scored region at at least one axial location along a longitudinal length thereof. The arm to can be configured to articulate or bend at weakened or scored region to allow the arm to move between the expanded and unexpanded configurations.

As in the illustrated embodiment shown in FIGS. 10 and 11, each arm 212 can include a plurality of links, modules, or segments, generally referred to herein as "segments," along a longitudinal length thereof. Each of the arms 212 includes eight segments, but the arms can include any number of segments. Adjacent segments can be movably coupled together such that each arm 212 can articulate or bend. Generally, the segments can allow each arm 212 to be configured as an articulating member configured to be positioned within a body cavity and articulate therein to define the working space 204, thereby pushing or retracting tissue facing the body cavity to improve access to the body cavity.

Each arm 212 can include a proximal segment 216p configured to attach the arm 212 to the hub 208, a distal segment 216d, and at least one mid-portion segment 216m located therebetween. Generally, the segments 216p, 216m, 216d can be movably coupled together to allow movement of the arm 212 between the expanded and unexpanded configurations. The segments 216p, 216m, 216d can have a variety of sizes, shapes, and configurations, and can be same or different from any of the other segments 216p, 216m, 216d. In the illustrated embodiment, each of the mid-portion segments 216m are identical, with the distal segment 216d and the proximal segment 216p being different from one another and from the mid-portion segments 216m. The segments 216p, 216m, 216d can be composed of any one or more flexible and/or rigid materials, although the segments 216p, 216m, 216d in the illustrated embodiment are substantially rigid and formed of at least one substantially rigid materials, e.g., stainless steel, titanium, etc. Optionally, the proximal segment 216p and/or the distal segment 216d can be formed of a material more rigid than a material forming the mid-portion segments 216m connected therebetween, which can help facilitate insertion of the arms 212 into a body cavity.

Generally, the segments 216p, 216m, 216d can each have a rectangular box shape such that the arm 212 can have a substantially constant outer diameter. In other exemplary embodiments, segments forming an arm can each have a cube shape, a triangular prism shape, a cylindrical shape, or any other shape. Outer-facing surfaces 216o of the segments 216p, 216m, 216d can be substantially planar or flat, which can facilitate pushing or retracting tissue using the expander member 210, as discussed further below. One or more of the outer-facing surfaces 216o can optionally include at least one gripping feature (not shown) formed thereon, e.g., a textured surface, at least one spiraling thread, etc., that can be configured to facilitate the segment's gripping of tissue and/or, if the flexible cover 224 is optionally included, the flexible cover 224 disposed around the arms 212.

A bore or lumen (not shown) can extend between proximal and distal ends of the proximal segment 216p and each of the mid-portion segments 216m. The distal segment 216d can also have a bore or lumen (not shown) extending therethrough, or the distal segment 216d can have a blind hole extending a partial distance therein from a proximal end of the distal segment 216d. Collectively, the bores of the proximal and mid-portion segments 216p, 216m and the bore or blind hole of the distal segment 216d can axially align with one another along a longitudinal axis of the arm 212 to form a channel configured to receive an actuator configured to move the arms 212 between the expanded and unexpanded configurations.

The actuator, which is shown in FIG. 11, can have a variety of sizes, shapes, and configurations. In an exemplary embodiment, the actuator can include a cable, string, thread, band, ribbon, strip, or wire 230, generally referred to herein as a "cable," extending from a proximal portion of the device 200, through the inner lumen 204 of the shaft 202, and through the bores in one arm's segments 216p, 216m to the arm's distal segment 216d. The device 200 can thus include an equal number of actuators and arms 212, as in the illustrated embodiment, that can be equally spaced apart from one another around a circumference of the shaft 202. In another embodiment, the device 200 can include a number of actuators less than a number of arms, such as if the arms are operatively coupled together such that movement of one arm causes similar movement of another arm. The actuators can be configured to be collectively actuated to move the arms 212 between the expanded and unexpanded configurations, e.g., be pulled to articulate the arms 212 to move the expander member 210 to the enlarged configuration and be released to move the expanded member 210 from the enlarged configuration to the relaxed configuration.

The segments 216p, 216m, 216d can be movably coupled together in any number of ways, e.g., by snap fit, by interference fit, by flexible connector positioned between adjacent segments, etc., as will be appreciated by a person skilled in the art. A flexible connector can include, e.g., a rubber or other elastomer configured to allow articulation of the segments relative to one another. In the illustrated embodiment, adjacent ones of the segments 216p, 216m, 216d are coupled together by snap fit with a proximal end of the distal segment 216d being received and snap fit within a distal end of a distal-most one of the mid-portion segments 216m, with a proximal end of a proximal-most one of the mid-portion segments 216m being received and snap fit with a distal end of the proximal segment 216p, and with the mid-portion segments 216p similarly linked together. A proximal end of the proximal segment 216p can be attached to the hub 208 in any way, such as by being snap fit into an opening or window 226, generally referred to herein as a "window," formed in the hub 208.

The mechanical insufflator 200 can include a lock mechanism configured to lock or hold the arms 212 in the expanded configuration, and thus also lock or hold the expander mechanism 210 in the expanded configuration. The lock mechanism can have a variety of configurations. Generally, the lock mechanism can be configured to engage the actuator and lock or hold the actuator in a position corresponding to the actuator causing the arms 212 to be in expanded configurations. As in the illustrated embodiment, the lock mechanism can be configured to engage each of the cables 230 extending through the inner lumen 204 and respectively coupled to each of the arms 212 such that the lock mechanism can lock the cables 230 in a fixed position to lock the arms 212 in expanded configurations, e.g., to lock the expander member 210 in the enlarged configuration. The lock mechanism can be located anywhere, such as within a device handle, the shaft 202 and/or the stop member 203. In the illustrated embodiment, the lock mechanism is located within the stop member 203 and hence obscured from view in FIG. 10. The stop member 203 can be configured to rotate about a longitudinal axis thereof, e.g., about a longitudinal axis 202A of the shaft 202, to selectively move the cables 230 proximally to tighten the cables 230 and expand the arms 212, and move the cables 230 distally to loosen the cables 230 and relax the arms 212. The stop member 203 can be configured to lock when the cables 230 are tightened with a lock mechanism, e.g., with a depressible button configured to fit within a hole formed in the shaft 202, with a gear-lock mechanism configured to be locked in a any one of a plurality of predetermined rotational positions, etc. The lock mechanism can be configured to lock the cables 230 when the arms 212 are fully articulated, as in the illustrated embodiment, or at any partial level of arm articulation.

Figure 13:
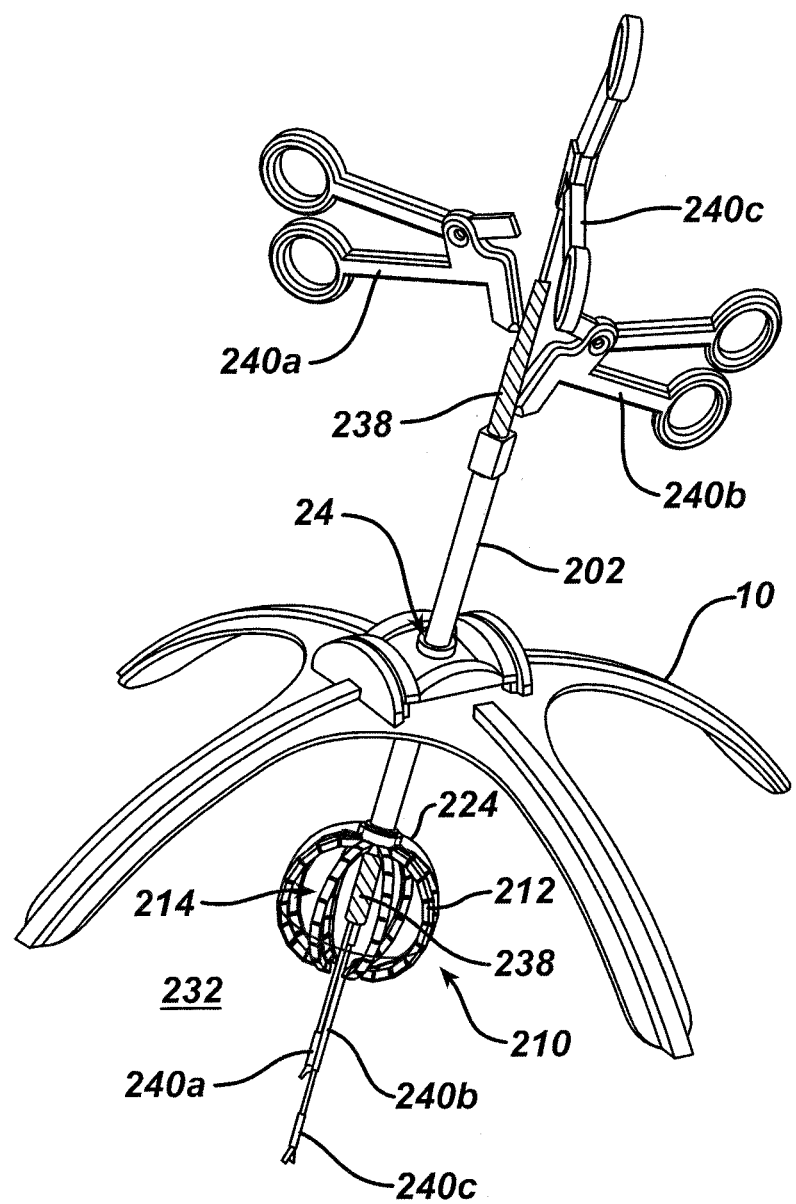
FIG. 13 is a perspective view of the mechanical insufflation device of FIG. 10 advanced through the surgical support system of FIG. 1 with a plurality of graspers advanced through the mechanical insufflation device such that distal ends of the graspers are positioned distally beyond a distal-most end of the mechanical insufflation device.
Figure 14:
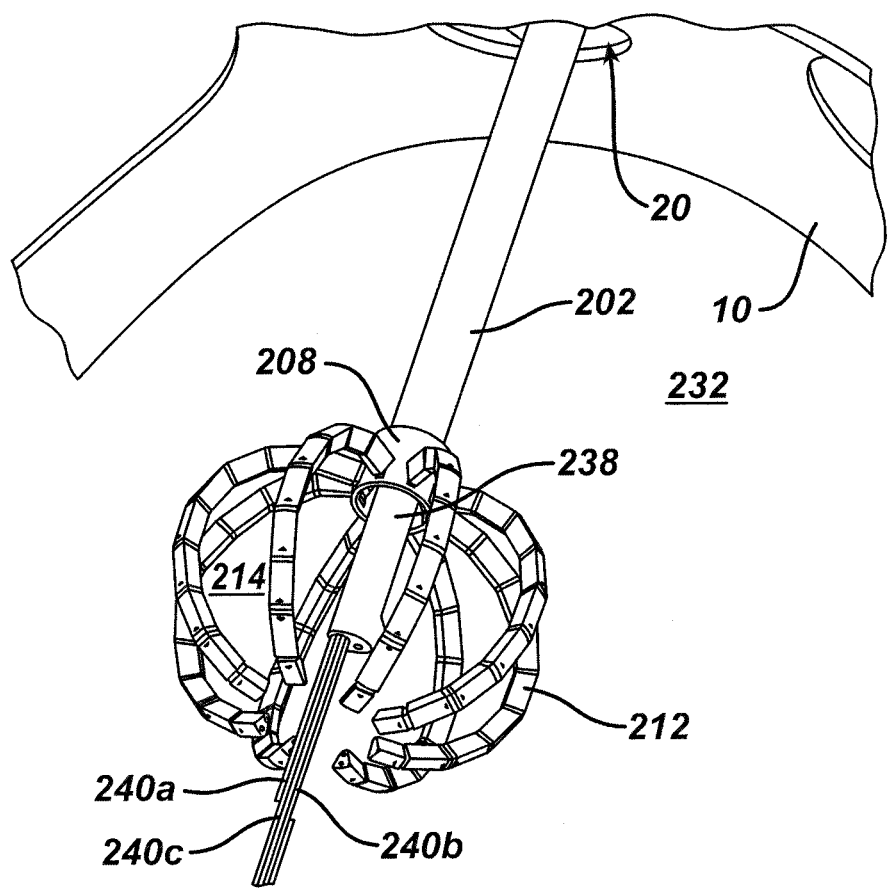
FIG. 14 is a perspective view of a distal portion of the mechanical insufflation device of FIG. 13 advanced through the surgical support system.

In use, the mechanical insufflator 200 can be used to mechanically insufflate a body cavity to provide open working space at a surgical site. In other words, the expander member 210 can be introduced into a body cavity and form the working space 204. As illustrated in one embodiment in FIGS. 13 and 14, a distal portion of the mechanical insufflator 200 can be introduced into a patient such that the expander member 210 can be positioned within a body cavity 232. Although the mechanical insufflation device 200 is shown in FIGS. 13 and 14 in use with the support 10 of FIG. 1, a person skilled in the art will appreciate that the mechanical insufflation device 200 can be used with any surgical support and that it can be used independently, e.g., without a surgical support. Optionally, a balloon (not shown) can be positioned over at least a distal portion of the arms 212 in the unexpanded configuration, which can help the arms 212 smoothly advance through a tissue opening. When the arms 212 are moved from the unexpanded configuration to the expanded configuration, the balloon can automatically break or pop off. The balloon can optionally be tethered or otherwise coupled to the mechanical insufflator such that after it breaks or pops off the arms 212, the balloon can remain attached to the mechanical insufflator 200 and be removed from the body cavity 232 simultaneously with the mechanical insufflator 200.

To position the expander member 210 within the body cavity 232, the support 10 can be positioned on an exterior tissue surface (not shown in FIGS. 13 and 14) as discussed above. The flexible cover 224 is absent from FIG. 14 for clarity. With the expander member 210 in the relaxed configuration, e.g., with the arms 212 in unexpanded configurations, the mechanical insufflator 200 can be advanced through the guide port 24 of the support 10 distal end first, through the exterior tissue surface, and into the body cavity 232 such that a distal end of the mechanical insufflator 200 can be positioned distal to an interior surface of the tissue. As discussed above, an incision can be pre-formed in the exterior tissue surface to ease passage of the device 200 through the skin. Also as discussed above, the guide port 24 can be adjusted before and/or after the mechanical insufflator 200 is advanced therethrough.

With the expander member 210 positioned within the body cavity 232, the actuator can be actuated, e.g., the cables 230 can be pulled proximally, to move the expander member 210 from the relaxed configuration to the enlarged configuration. So moving the expander member 210 also moves the arms 212 from the unexpanded configuration to the expanded configuration and forms the working space 204, as discussed above. Any tissue surrounding an exterior of the expander member 210 can therefore be pushed or retracted in a direction generally away from the working space 204 so as to clear the working space 204, which can ease visualization and performance of a surgical procedure as well as help prevent the surrounding tissue from interfering with the surgical procedure. No pushed or retracted tissue is shown in FIGS. 13 and 14 for clarity. The arms 212 can be locked in the expanded configuration, as discussed above.

With the arms 212 in the expanded configuration, a second surgical instrument 238 can be advanced through the guide port 24 distal end first, through the exterior tissue surface, and into the underlying body cavity 232. In an exemplary embodiment, the second instrument 238 can be inserted through the mechanical insufflator's inner lumen 204 such that a distal end of the second instrument 238 can be positioned within the working space 214 in the body cavity 232. The second instrument 238 in the illustrated embodiment includes a rigid cannula having a plurality of working channels extending therethrough, but any instrument can be used.

The second instrument 238 can optionally be advanced distally beyond the working space 214 if distal ends of the arms 212 are configured to not contact one another as in the illustrated embodiment. In other words, while the arms 212 can be configured to converge toward the longitudinal axis 202A of the shaft 202 when in the expanded configuration, the arms 212 can be configured to not directly contact one another when in the expanded configuration, as shown in FIGS. 10, 11, 13, and 14. The working space 214 can thus have an open distal end configured to allow passage of an instrument or other matter, e.g., tissue, fluid, etc., therethrough into and/or out of the working space 214. The distal end of the second instrument 238 is positioned within the working space 214 in FIGS. 13 and 14. However, FIGS. 13 and 14 also illustrate three additional surgical instruments 240a, 240b, 240c advanced through the working channels of the second instrument 238, with distal ends of each of the additional instruments 240a, 240b, 240c extending distally beyond the working space 214 and distally beyond the device 200. The three additional instruments 240a, 240b, 240c each includes graspers having opposed movable jaws, but any instruments can be advanced through the second instrument 238.

As discussed above, an instrument advanced through the guide port 24 can be pivoted about the pivot point defined by the guide port 24. The mechanical insufflator 200, with or without any or all of the optional instruments 238, 240a, 240b, 240c advanced therethrough, can be pivoted about the pivot point to selectively position the device's distal end, e.g., to selectively position the expander member 210 within the body cavity 232. Similarly, any or all of the instruments 238, 240a, 240b, 240c can be moved to pivot about the pivot point.

Before and/or after the mechanical insufflator 200 has been positioned within the body cavity 232, an insufflation fluid can optionally be introduced into the body cavity 232 to fluidly insufflate the body cavity 232. The insufflation fluid can provide insufflation in addition to the mechanical insufflator. If insufflation fluid is introduced into the body cavity, a seal positioned within the shaft 202 can help prevent the insufflation fluid from escaping the patient's body through the mechanical insufflator 200.

The mechanical insufflator 200 can be removed from the body cavity 232 by moving the arms 212 from the expanded configuration to the unexpanded configuration such that the expander member 210 reduces in diameter from a diameter larger than the guide port's diameter to a diameter less than the guide port's diameter so as to fit through the guide port 24. Although the mechanical insufflator 200 can be removed from the body cavity 232 with the arms 212 in the expanded configuration, moving the arms 212 to the unexpanded configuration before removing the arms 212 from the patient can help reduce trauma and risk of injury to the patient.

Figure 15:
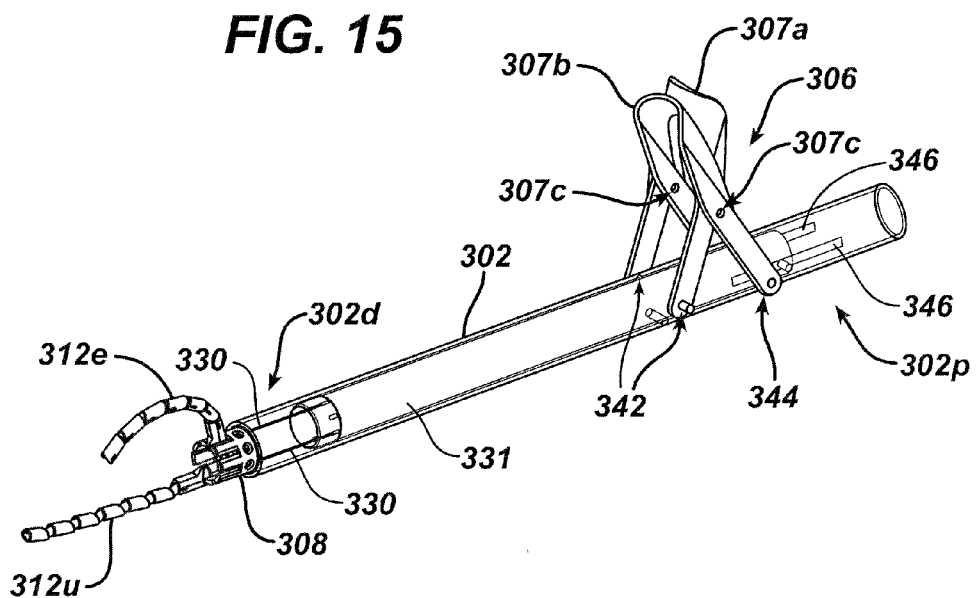
FIG. 15 is a perspective view of another embodiment of a mechanical insufflation device having a plurality of arms.
Figure 16:
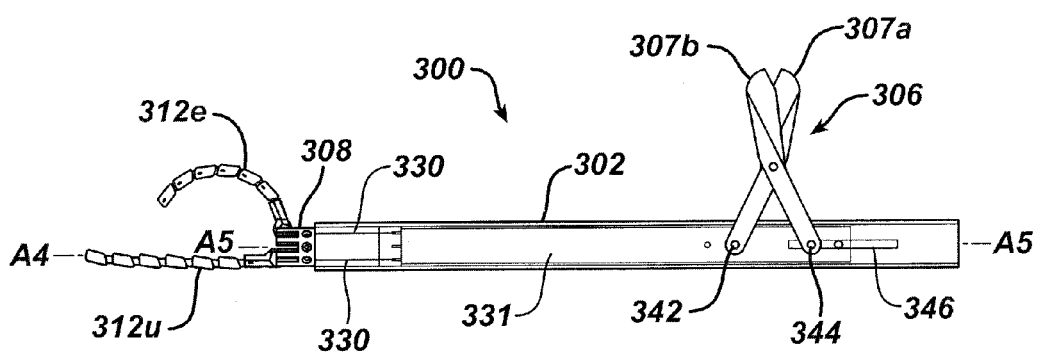
FIG. 16 is a side view of the mechanical insufflation device of FIG. 15.
Figure 17:
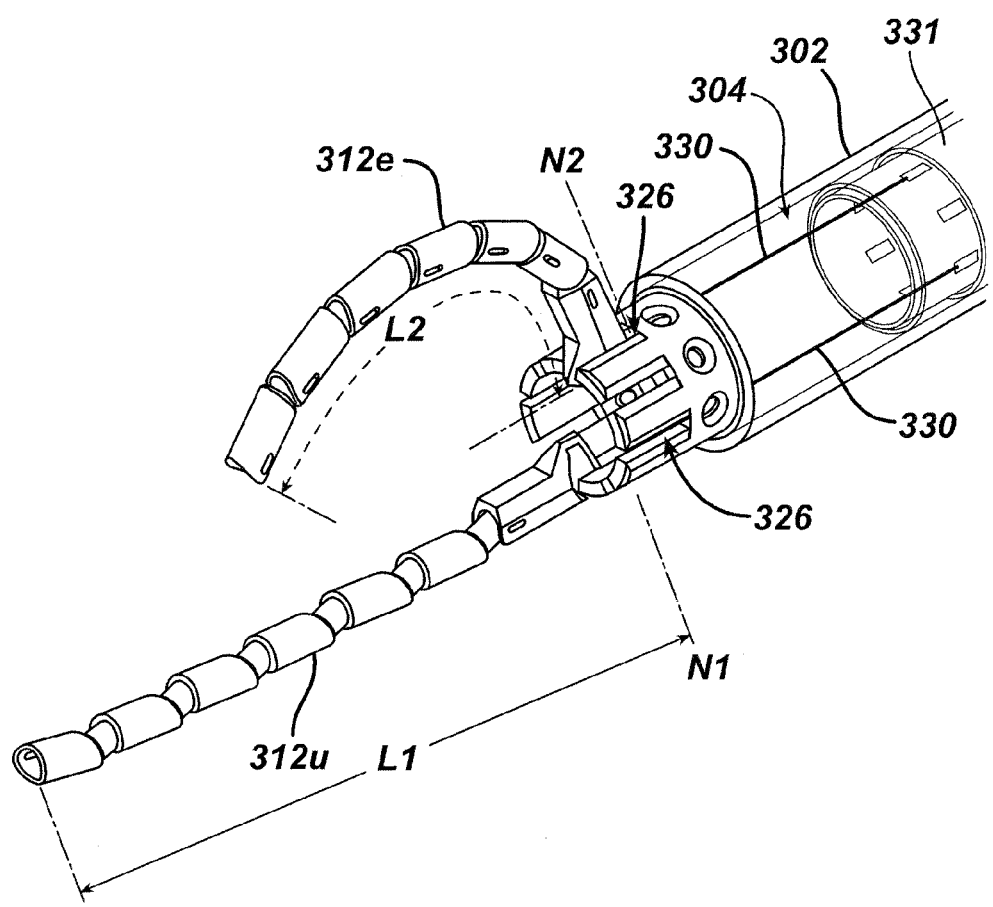
FIG. 17 is a perspective view of a distal portion of the mechanical insufflation device of FIG. 15.

FIGS. 15-17 illustrate another embodiment of a mechanical insufflator 300. The mechanical insufflator 300 can generally be configured and used similar to the mechanical insufflator 200 of FIGS. 10, 11, 13, and 14. The mechanical insufflator 300 can include a handle 306 at a proximal end thereof, and an expander member at a distal end thereof and having a plurality of arms, although only two arms 312e, 312u of the expander member are illustrated in FIGS. 15-17. One of the arms 312e is shown in an expanded configuration, and one of the arms 312u is shown in an unexpanded configuration, although in an exemplary embodiment, all arms of an expander member are simultaneously in the same configuration, e.g., are either expanded or unexpanded. As also shown in FIG. 18, an arm can include a proximal segment 316p, a distal segment 316d, and at least one mid-portion segment 316m located therebetween. FIG. 19 also illustrates the proximal segment 316p and mid-portion segments 316m.

The arm and segments 316p, 316m, 316d can generally be configured and used similar to the arm 212 and segments 216p, 216m, 216d of FIGS. 10 and 11 such that the segments 316p, 316m, 316d can be movably coupled together to allow the arms to move between the expanded and unexpanded configurations. In this illustrated embodiment, the segments 316p, 316m, 316d can be cammed together to allow relative movement between the segments 316p, 316m, 316d. The segments 316p, 316m, 316d cammed together with a proximal end of the distal segment 316d including a male member 318d configured to be received in a distal female member 320m of a distal-most one of the mid-portion segments 316m. Similarly, proximal ends of each of the mid-portion segments 316m can include a male member 318m configured to be received in a distal female member of another segment, either a distal female member 320m of another mid-portion segment 316m or, for a proximal-most one of the mid-portion segments 316m, a distal female member 320p of the proximal segment 316p. Although, as will be appreciated by a person skilled in the art, the male and female members of the various segments can have a variety of sizes, shapes, and configurations, the male members 318d, 318m in the illustrated embodiment are substantially cylindrical and configured to securely fit within substantially ovular female members 320m, 320p. The size and shape of the female members 320m, 320p can be configured to allow the male members 318d, 318m to move or slide therein, as in the illustrated embodiment, which can facilitate movement of the arms 312 between the expanded and unexpanded configurations.

A spring 319 can be positioned adjacent the male members 318d, 318m (the spring is obscured for the distal male member 318d). The springs 319 of an arm can collectively be configured to bias the arm to the unexpanded configuration. The springs 319 of an arm can also be configured to urge adjacent segments in an arm away from one another when the arm is in the unexpanded configuration. When an arm moves from the unexpanded configuration to the expanded configuration, the springs 319 can compress such that adjacent segments move toward one another. In other words, as shown in FIG. 17, a longitudinal length L1 of the arm 312u in the unexpanded configuration can be greater than a longitudinal length L2 of the arm 312e in the expanded configuration.

The proximal segment 316p can also include a coupler member 322 configured to couple to a hub 308 formed at a distal end of a shaft 302 of the mechanical insufflator 300. The mechanical insufflator 300 can generally be configured and used similar to the mechanical insufflator 200 of FIG. 10. The coupler member 322 can have a variety of sizes, shapes, and configurations. Generally, the coupler member 322 can be configured to seat in the hub 308 to secure the arm 312 thereto. In the illustrated embodiment, the coupler member 322 includes a protrusion having a complementary shape to a window 326 such that the coupler member 322 can mate thereto by interference or snap fit. When an arm moves from the unexpanded configuration to the expanded configuration, the proximal segment 316p can be configured to slide proximally within the window 326, e.g., from a proximal-most position N1 to a proximal-most position N2 illustrated in FIG. 19. In this way, all of the segments 316d, 316p, 316m can be configured to be positioned as distally far down as possible while still being coupled to the hub 308, which can help reduce a diameter of the expander member when the arms are not expanded. The arm 312u in the unexpanded configuration has a longitudinal axis A4 that is substantially straight, as shown in FIG. 18, such that, as mentioned above, longitudinal axes of the arms can be substantially parallel to one another when the arms 312 are each articulated to form an expander member in the enlarged configuration. Similarly, the longitudinal axis A4 of the arm 312u in the unexpanded configuration can be substantially parallel to a longitudinal axis A5 of the shaft 302.

The mechanical insufflator 300 can also include an actuator configured to move the arms between the expanded and unexpanded configurations. In the illustrated embodiment, the actuator includes a plurality of cables 230 each associated with one of the mechanical insufflator's arms, and an elongate tube 331. Only two cables 230 are illustrated in FIGS. 15-17, because only two of the device's arms are shown. A distal end of each of the cables 330 can be attached to its associated arm, and a proximal end of each of the cables 330 can be attached to a distal end of the elongate tube 331. The elongate tube 331 can extend through an inner lumen 304 of the shaft 302 and be configured to be slidably movable therein. Generally, sliding the elongate tube 331 proximally relative to the shaft 302 can pull or tension the cables 330, which can move the arms from the unexpanded configuration to the expanded configuration. Conversely, sliding the elongate tube 331 distally relative to the shaft 302 can relax the cables 330, which can move the arms from the expanded configuration to the unexpanded configuration. A proximal end of the elongate tube 331 can be coupled to the handle 306. The handle 306 can thus be configured to move the elongate tube 331 and the cables 330, e.g., to actuate the actuator.

The handle 306 can have a variety of sizes, shapes, and configurations, as will be appreciated by a person skilled in the art. As in the illustrated embodiment, the handle 306 can include first and second handholds 307a, 307b. The first and second handholds 307a, 307b can be pivotally coupled to one another at handle pivot points 307c. The first handhold 307a can be pivotally coupled to the shaft 302 at a first pivot points 342, as shown in FIG. 15. The second handhold 307b can be pivotally coupled to the elongate tube 331 at second pivot points 344, as also shown in FIG. 15 (one of the second pivot points 344 is obscured in FIG. 15). The shaft 302 can have opposed slots 346 formed in sidewalls thereof to allow the second handhold 307b to couple to the elongate tube 331 at the second pivot points 344. The first pivot points 342 can therefore be in a fixed relative to the shaft 302 but in a variable position relative to the elongate tube 331. Conversely, the second pivot points 344 can be in a fixed position relative to the elongate tube 331 but in a variable position relative to the shaft 302. When the second pivot points 344 are at a distal-most position within the slots 346, the arms can be in an unexpanded configuration. When the handle 306 is manipulated, e.g., the handholds 307a, 307b are pivoted relative to one another at the handle pivot point 307c, the handholds 307a, 307b can move toward the shaft 302 with the first handhold 307a pivoting about the first pivot points 342 and the second handhold 307b pivoting about the second pivot points 344. As the second handhold 307b pivots about the second pivot points 344, the second pivot points 344 can move proximally along the slots 346, and the elongate tube 331 can move in a proximal direction, thereby pulling the cables 330 such that the arms can move from the unexpanded to the expanded configuration.

When the second pivot points 344 are in a proximal-most position, the handholds 307a, 307b can be configured to lock at the handle pivot point 307c, thereby holding or locking the arms in the expanded configuration. In the illustrated embodiment the handholds 307a, 307b are configured to automatically or self-lock when the handle pivot point 307c moves distally beyond a mid-point between the first and second pivot points 342, 344. The handholds 307a, 307b can be released from a locked position by pulling them up such that the handholds 307a, 307b pivot relative to one another at the handle pivot point 307c, the first handle 307a pivots about the first pivot point 342, and the second handhold 307b pivots about the second pivot point 344, which can slide distally in the slots 346 to move the arms from the expanded to the unexpanded configuration. In some embodiments, as will be appreciated by a person skilled in the art, the handholds 307a, 307b can be configured to lock in a plurality of positions, e.g., with a rack and pawl mechanism, to allow the arms to be locked in when not fully expanded.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a mechanical insufflator arm, a flexible cover, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   positioning a surgical support system on an exterior tissue surface of a patient such that an instrument guide port of the surgical support system is positioned a distance remote from the tissue surface, the instrument guide port defining a pivot point at the distance remote from the tissue surface;
   advancing a surgical instrument through the instrument guide port such that a shaft of the surgical instrument extends through a tissue opening formed in the tissue surface to position a distal end of the instrument at a first position within a body cavity underlying the tissue surface; and
   angularly adjusting the instrument relative to the surgical support system such that the instrument pivots at the pivot point to move the pivot point in two planes of motion and to move the distal end of the instrument in three planes of motion from the first position within the body cavity to a second, different position within the body cavity, the pivoting of the instrument being limited to movement in the two planes of motion.

2. The method of claim 1, further comprising, while the surgical support system remains in contact with the tissue surface, moving the instrument guide port to a different location such that the pivot point is located a second, different distance remote from the tissue surface.

3. The method of claim 1, further comprising, with the distal end of the instrument in one of the first and second positions, locking the instrument in a fixed position relative to the instrument guide port, thereby locking the distal end of the instrument in the one of the first and second positions.

4. The method of claim 3, wherein the distal end of the instrument locked in the one of the first and second positions is prevented from moving in an x dimension and in a y dimension, and is prevented from rotating about a longitudinal axis of the shaft of the instrument.

5. The method of claim 1, further comprising, when the distal end of the instrument is positioned within the body cavity, increasing a volume of a working area within the body cavity by expanding a plurality of movable arms at the distal end of the instrument.

6. A surgical method, comprising:
   positioning a surgical support on an exterior skin surface overlying a body cavity, the support including distal and proximal portions movably coupled together;
   inserting a surgical instrument through a guide in the proximal portion of the support and through an opening in the skin surface to position a distal end of the surgical instrument within the body cavity at a first location; and
   moving the proximal portion of the support in a linear direction relative to the distal portion of the support and in an arcuate direction relative to the distal portion of the support to move the distal end of the surgical instrument from the first location to a second, different location within the body cavity.

7. The method of claim 6, wherein moving the proximal portion of the support in the linear direction moves the proximal portion in a first dimension relative to the distal portion, and moving the proximal portion of the support in the arcuate direction moves the proximal portion in second and third dimensions relative to the distal portion.

8. The method of claim 6, wherein the proximal portion of the support includes an arcuate support, and wherein moving the proximal portion in the arcuate direction comprises moving the proximal portion along the arcuate support.

9. The method of claim 6, further comprising, with the distal end of the instrument in one of the first and second locations, locking the instrument in a fixed position relative to the guide, thereby locking the distal end of the instrument in the one of the first and second locations.

10. The method of claim 6, further comprising advancing a second surgical instrument through a second guide in the proximal portion of the support to advance a distal end of the second instrument through the opening in the skin surface and into the body cavity.

11. The method of claim 10, wherein moving the proximal portion of the support causes the distal end of the second instrument to move from a third location within the body cavity to a fourth, different location within the body cavity.

12. The method of claim 6, wherein moving the proximal portion of the support in the linear direction relative to the distal portion comprises sliding the proximal portion.

13. The method of claim 6, wherein moving the proximal portion of the support in the arcuate direction relative to the distal portion comprises sliding the proximal portion.

14. The method of claim 6, wherein moving the portion of the support in the linear direction causes the distal end of the surgical instrument to move in a first dimension, and moving the portion of the support in the arcuate direction causes the distal end of the surgical instrument to move in second and third dimensions.

15. The method of claim 14, wherein the first and second dimensions are perpendicular to one another.

16. The method of claim 1, wherein the two planes of motion are perpendicular to one another.

* * * * *